(12) United States Patent
Ablordeppey

(10) Patent No.: US 12,006,301 B1
(45) Date of Patent: Jun. 11, 2024

(54) AND SYNTHESIS OF DUAL 5-HT1A AND 5-HT7 RECEPTOR LIGANDS

(71) Applicant: Florida A&M University, Tallahassee, FL (US)

(72) Inventor: Seth Y. Ablordeppey, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 17/732,018

(22) Filed: Apr. 28, 2022

Related U.S. Application Data

(60) Provisional application No. 63/188,418, filed on May 13, 2021.

(51) Int. Cl.
  *C07D 401/04* (2006.01)
  *C07D 401/12* (2006.01)
  *C07D 401/14* (2006.01)

(52) U.S. Cl.
  CPC .......... *C07D 401/04* (2013.01); *C07D 401/12* (2013.01); *C07D 401/14* (2013.01)

(58) Field of Classification Search
  CPC .................................................. C07D 401/14
  See application file for complete search history.

(56) References Cited

U.S. PATENT DOCUMENTS

| 4,339,580 A * | 7/1982 | Kikumoto .......... C07D 295/088 544/360 |
| 2007/0027138 A1 | 2/2007 | Jordis et al. |

FOREIGN PATENT DOCUMENTS

| BE | 655442 A | * | 6/1965 |
| FR | 2138488 A1 | * | 1/1973 |
| WO | 2018148529 A1 | | 8/2018 |

OTHER PUBLICATIONS

New Psychotherapeutic Agent, Chlordiazepoxide Tobin et al. JAMA. 1960;174(10):1242-1249. doi:10.1001/jama.1960.03030100010003 (Year: 1960).*
Estimation of psycholeptic and psychoanaleptic medicine use in an adult general population sample using the Anatomical Therapeutic Chemical classification John et al. Int. J. Methods Psychiatr. Res. 17(4): 220-231 (2008) (Year: 2008).*
Ofori, Edward et al. New dual 5-HT1A and 5-HT7 receptor ligands derived from SYA16263. European Journal of Medicinal Chemistry, 214 (Feb. 3, 2021) 113243.
Bantick, R.A. et al. The 5-HT1A receptor in schizophrenia: a promising target for novel atypical neuroleptics? J. Psychopharmacol. 15 (1) (2001) 37-46.
Rollema, H. et al. Clozapine increases dopamine release in prefrontal cortex by 5-HT1A receptor activation, Eur. J. Pharmacol. 338 (2) (1997) R3-R5.
Ohno, Yukihiro. New insight into the therapeutic role of 5-HT1A receptors in central nervous system disorders, Cent. Nerv. Syst. Agents Med. Chem. 10 (2) (2010) 148-157.
Ramboz, S. et al. Serotonin receptor 1A knockout: an animal model of anxiety-related disorder, Proc. Natl. Acad. Sci. U. S. A 95 (24) (1998) 14476-14481.
Heisler, L.K. et al. Elevated anxiety and antidepressant-like responses in serotonin 5-HT1A receptor mutant mice, Proc. Natl. Acad. Sci. U. S. A 95 (25) (1998) 15049-15054.
Wang, S-M et al. Vilazodone for the treatment of depression: an update, Chonnam Med. J. 52 (2) (2016) 91-100.
Frampton, J.E. Vilazodone: in major depressive disorder, CNS Drugs 25 (7) (2011) 615-627.
Modica, M.N. et al. Structure-activity relationships and therapeutic potentials of 5-HT(7) receptor ligands: an update, J. Med. Chem. 61 (19) (2018) 8475-8503.
Hedlund, P.B. and J. G. Sutcliffe. Functional, molecular and pharmacological advances in 5-HT7 receptor research, Trends Pharmacol. Sci. 25 (9) (2004) 481-486.
Roberts, A.J. and P.B. Hedlund. The 5-HT(7) receptor in learning and memory, Hippocampus 22 (4) (2012) 762-771.
Abbas, A.I. et al. Amisulpride is a potent 5-HT7 antagonist: relevance for antidepressant actions in vivo, Psychopharmacology 205 (1) (2009) 119-128.
Naumenko, V.S. et al. Interplay between serotonin 5-HT1A and 5-HT7 receptors in depressive disorders, CNS Neurosci. Ther. 20 (7) (2014) 582-590.
Hoyer, D. et al. Molecular, pharmacological and functional diversity of 5-HT receptors, Pharmacol. Biochem. Behav. 71 (4) (2002) 533-554.
Renner, U. et al. Heterodimerization of serotonin receptors 5-HT1A and 5-HT7 differentially regulates receptor signalling and trafficking, J. Cell Sci. 125 (Pt 10) (2012) 2486-2499.
Fischer, J. et al. Successful drug discovery vol. 3, ChemMedChem 13 (18) (2018), 2011.
Rague, A. and K. Tidgewell. Pharmacophore comparison and development of recently discovered long chain arylpiperazine and sulfonamide based 5-HT7 ligands, Mini Rev. Med. Chem. 18 (7) (2018) 552-560.
Peprah, K. et al. Multireceptor drug design: haloperidol as a scaffold for the design and synthesis of atypical antipsychotic agents, Bioorg. Med. Chem. 20 (3) (2012) 1291-1297.
Sampson, D. et al. Identification of a new selective dopamine D4 receptor ligand, Bioorg. Med. Chem. 22 (12) (2014) 3105-3114.
Bricker, B.A. et al. Evaluation of SYA16263 as a new potential antipsychotic agent without catalepsy, Pharmacol. Biochem. Behav. 179 (2019) 55-62.
Ofori, E. et al. Synthesis and evaluation of the structural elements in alkylated tetrahydroisoquinolines for binding to CNS receptors, Bioorg. Med. Chem. 24 (22) (2016) 5730-5740.
Peprah, K. et al. Structure-activity relationship studies of SYA 013, a homopiperazine analog of haloperidol, Bioorg. Med. Chem. 20 (5) (2012) 1671-1678.
Onyameh, E.K. et al. Enantioseparation of 5-chloro-2-{2-[3,4-dihydroisoquinoline-2(1H)-yl]ethyl}-2-methyl-2,3- dihydro-1H-inden-1-one (SYA 40247), a high-affinity 5-HT(7) receptor ligand, by HPLC-PDA using amylose tris-(3, 5-dimethylphenylcarbamate) as a chiral stationary phase, Biomed. Chromatogr. 33 (9) (2019), e4565.

(Continued)

*Primary Examiner* — Jeffrey S Lundgren
*Assistant Examiner* — Eric Tran
(74) *Attorney, Agent, or Firm* — Michele L. Lawson; Smith & Hopen, P.A.

(57) ABSTRACT

Novel dual 5-HT1A and 5-HT7 receptor ligands and methods of using the novel ligands to treat a neurological disorder are presented.

20 Claims, 10 Drawing Sheets

(56) References Cited

OTHER PUBLICATIONS

Ofori, E. et al. Design and synthesis of dual 5-HT1A and 5-HT7 receptor ligands, Bioorg. Med. Chem. 24 (16) (2016) 3464-3471.
Shapiro, D.A. et al. Aripiprazole, a novel atypical antipsychotic drug with a unique and robust pharmacology, Neuropsychopharmacology 28 (8) (2003) 1400-1411.

* cited by examiner

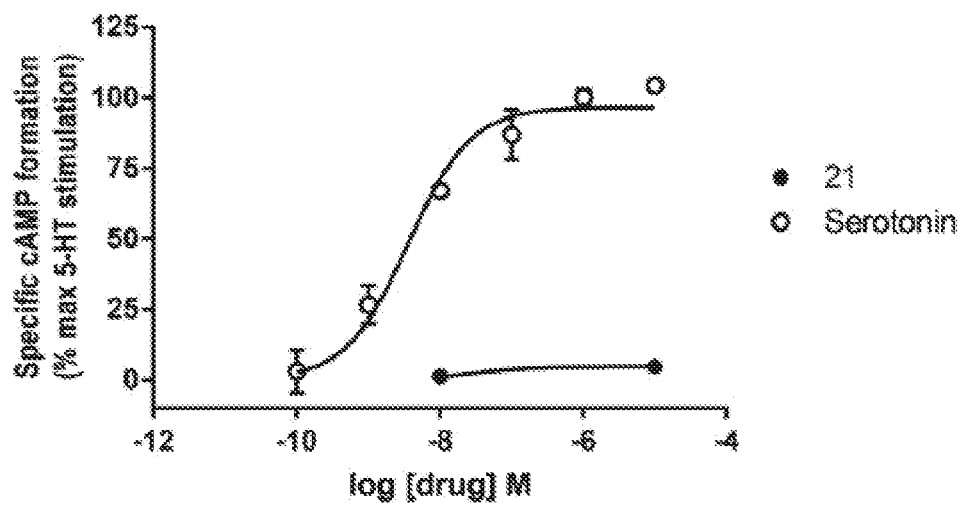
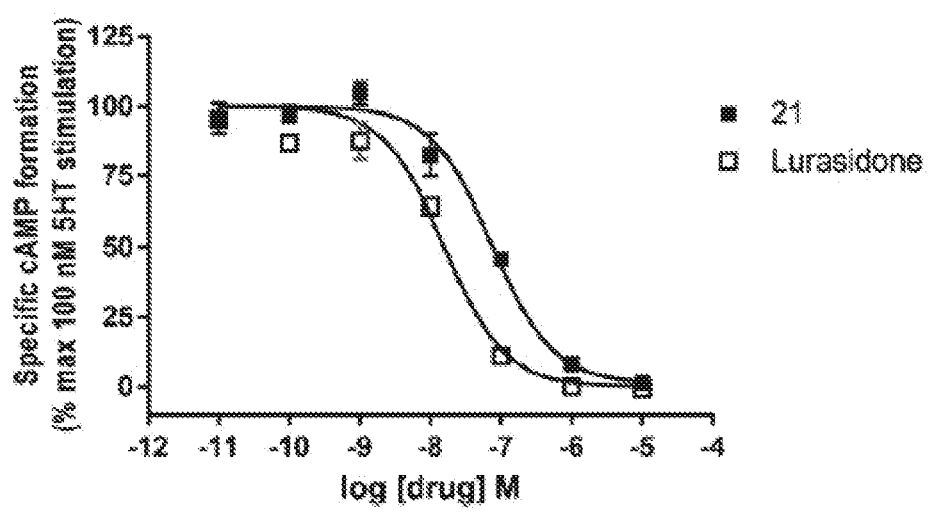
FIG. 15A-B

AND SYNTHESIS OF DUAL 5-HT1A AND 5-HT7 RECEPTOR LIGANDS

CROSS REFERENCE TO RELATED APPLICATIONS

This application is a nonprovisional of and claims priority to U.S. Provisional Patent Application Ser. No. 63/188,418, entitled "Design and Synthesis of Dual 5-$HT_{1A}$ and 5-HT7 Receptor Ligands", filed May 13, 2021, the contents of which are hereby incorporated by reference into this disclosure.

GOVERNMENT SUPPORT

This invention was made with Government support under Grant No. 2SC1GM116724 awarded by the National Institutes of Health (NIH). The Government has certain rights in the invention.

FIELD OF INVENTION

This invention relates to compounds and methods of treatment for neurological disorders. Specifically, the invention provides novel compounds and methods of treatment for cognitive and anxiolytic impairments in neurological disorders such as depression, anxiety, schizophrenia, and Alzheimer's disease.

BACKGROUND OF THE INVENTION

The pharmacotherapy of major central nervous system (CNS) disorders relies on multi-CNS receptor targeting. In fact, atypical antipsychotic agents such as cariprazine, aripiprazole, clozapine, ziprasidone, and lurasidone owe their superior efficacy and tolerable side-effect profiles to their ability to modulate dopamine (DA), serotonin (5-HT), and even cholinergic (ACh) receptors simultaneously [1-3].

Serotonin receptors (5-HTRs) are found predominantly on neurons in the dorsal and median raphe nuclei of the brainstem that project into other brain regions such as the hypothalamus, thalamus, hippocampus, and cortex where they regulate mood, perception, reward, anger, aggression, appetite, memory, sexuality, and attention [4-6]. Not surprisingly, perturbation in serotonergic neurotransmission is implicated in several neuropsychiatric illnesses including major depressive disorder (MDD), bipolar disorder, anxiety, attention deficit and hyperactivity disorder (ADHD) and schizophrenia [7,8]. Several lines of evidence have revealed that the 5-$HT_{1A}$ receptor subtype (5-$HT_{1A}$R) is involved in the pathophysiology of the aforementioned mental disorders making it a tenable target for antidepressant, antianxiety and antipsychotic drug discovery. For instance, there is a growing body of evidence that supports the anti-negative symptom and pro-cognitive effects of ligands that activate 5-$HT_{1A}$R in schizophrenia [9-11]. In addition, 5-$HT_{1A}$ knockout mice display increased anxiety and depressive behaviors and have been used as animal models for these disorders, further highlighting the key roles that the 5-$HT_{1A}$R plays in the pathophysiology of CNS disorders [12,13]. In fact, antidepressants such as vilazodone that inhibit 5-HT reuptake and partially activate 5-$HT_{1A}$Rs are more efficacious, fast acting, and tolerable [14,15].

Another closely related 5-HTR, the serotonin-7 receptor (5-HT7R), mediates key physiological functions that include sleep, mood, learning memory and cognition [16-19]. Indeed, the antidepressant effects of amisulpride are attributed to its antagonism at the 5-HT7 receptor [20]. A growing wealth of evidence suggests that 5-HT7 is co-localized with 5-$HT_{1A}$, and cross talks resulting from heterodimers of these receptors have been implicated in CNS diseases such as depression [21]. Not only do these receptors share over 40% sequence homology, ligands that activate these receptors tend to exhibit cross activity [22,23]. Dual ligands that activate 5-$HT_{1A}$ and antagonize 5-HT7 receptors may serve as potential treatment options for depression, anxiety and other diseases characterized by cognitive deficits.

N-Aryl/heteroaryl piperazines are of interest due in part to their unique ability to impart desirable pharmacological properties to clinically useful CNS drugs including aripiprazole and cariprazine (FIG. 1) [24]. In fact, evidence from pharmacophore models suggests that the pyridinyl-piperazine moiety may provide key structural elements necessary for binding to both 5-$HT_{1A}$ and 5-HT7 [25]. In the inventor's previous publications [26,27], the deoxygenated azaperone SYA 16263 (Compound 2) was identified as a ligand that displayed a desirable in-vitro binding affinity profile to clinically relevant CNS receptors. (FIG. 1). In animal studies, SYA 16263 possesses moderate antipsychotic-like activity with low propensity to cause motoric side effects [28]. The inventors reported in a recent patent [29] that, as a possible mechanism of action, compound 2 displayed a biased β-arrestin functionality at the D2 receptor. However, compound 2 also displayed a very high affinity at the 5-$HT_{1A}$R, sparking the interest in exploring its structure-affinity relationship (SAFIR) at relevant CNS receptors and further expand and probe the potential utility of its analogs in CNS diseases. To that end, the inventors have designed, synthesized, and evaluated several N-alkyl substituted pyridinyl-piperazines to identify new leads for further development.

SUMMARY OF INVENTION

Diseases that affect the central nervous system are complex in their etiology and treatment options with single biological targets often treat only some symptoms and not others. Thus, current trends are focused on multiple targeting strategies. The inventors have previously reported that dual 5-$HT_{1A}$ and 5-HT7 receptor ligands might find utility as treatment options for various CNS related conditions including cognitive and anxiolytic impairments. The inventors have also more recently reported that SYA16263 has antipsychotic-like properties with an absence of catalepsy in animal models ascribed to its ability to recruit β-arrestin to the D2 receptor. However, SYA16263 also binds with very high affinity to 5-$HT_{1A}$R (Ki=1.1 nM) and a moderate affinity at 5-HT7R (Ki=90 nM).

Using SYA16263 as the lead molecule, the inventors have conducted a limited structure-affinity relationship (SAFIR) study resulting in the identification of a new dual 5-$HT_{1A}$R and 5-HT7R ligand, 6-chloro-2-methyl-2-(3-(4-(pyridin-2-yl)piperazin-1-yl)propyl)-2,3-dihydro-1H-inden-1-one, which unlike SYA16263, has a sub-nanomolar (5-$HT_{1A}$R, Ki=0.74 nM) and a low nanomolar (5-HT7R, Ki=8.4 nM) affinity for these receptors. Interestingly, this compound is a full agonist at 5-$HT_{1A}$R and an antagonist at the 5-HT7R, functional characteristics which point to its potential as an antidepressant agent.

These new compounds can be used in the development of novel drugs for the treatment of depression, anxiety or cognitive impairments associated with several mental illnesses such as schizophrenia and Alzheimer's disease.

In an embodiment, a compound is presented comprising Formula (I), (II), (III), or (IV):

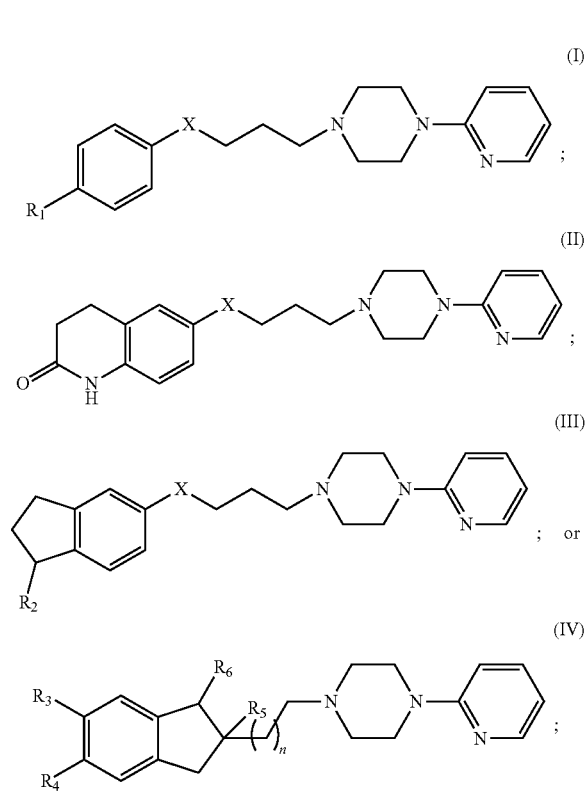

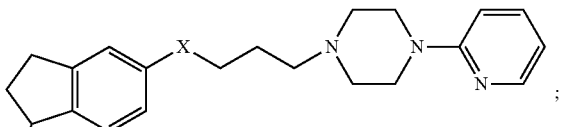

wherein X is C=O, CH$_2$, or O;
wherein R$_1$ is AcHN or NH$_2$;
wherein R$_2$ is H or =O;
wherein R$_3$ is Cl or H;
wherein R$_4$ is Cl, F, I, Br or H;
wherein R$_5$ is CH$_3$ or H;
wherein R$_6$ is =O, H or OH; and
wherein n is an integer from 1 to 3.

In an embodiment, the compound comprises Formula (IV), wherein R$_3$ is H, R$_4$ is Cl, R$_5$ is CH$_3$, R$_6$ is =O and n is 2.

In another embodiment, a composition for treating a neurological disorder is presented comprising: a compound comprising Formula (I), (II), (III), or (IV):

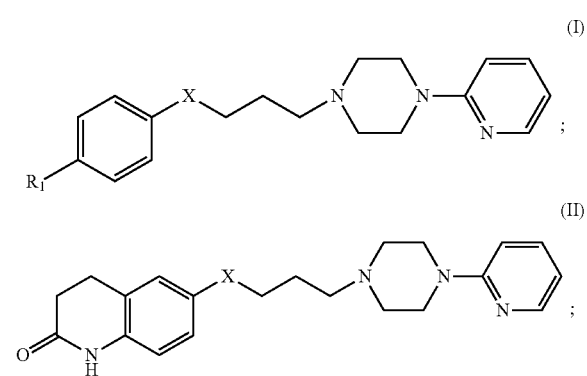

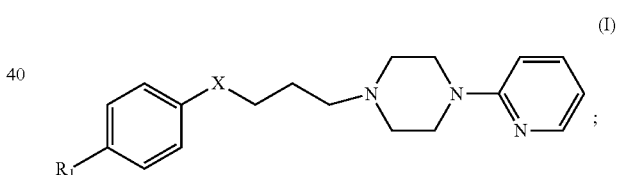

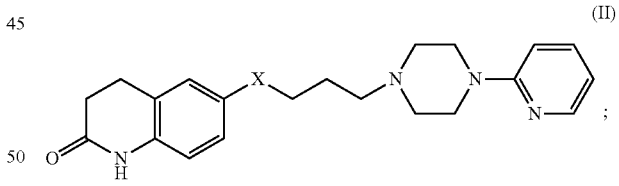

wherein X is C=O, CH$_2$, or O;
wherein R$_1$ is AcHN or NH$_2$;
wherein R$_2$ is H or =O;
wherein R$_3$ is Cl or H;
wherein R$_4$ is Cl, F, I, Br or H;
wherein R$_5$ is CH$_3$ or H;
wherein R$_6$ is =O, H or OH;
wherein n is an integer from 1 to 3; and
a pharmaceutically acceptable carrier.

In an embodiment, the composition comprises a compound of Formula (IV), wherein R$_3$ is H, R$_4$ is Cl, R$_5$ is CH$_3$, R$_6$ is =O and n is 2.

In a further embodiment, a method of treating a neurological disorder in a patient in need thereof is presented comprising: administering a therapeutically effective amount of a composition to a patient in need thereof, the composition comprising a compound comprising Formula (I), (II), (III), or (IV):

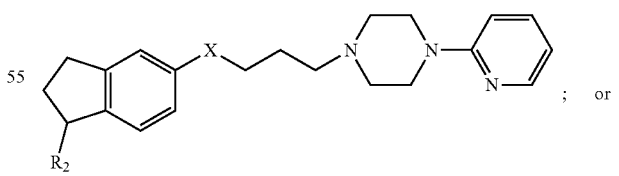

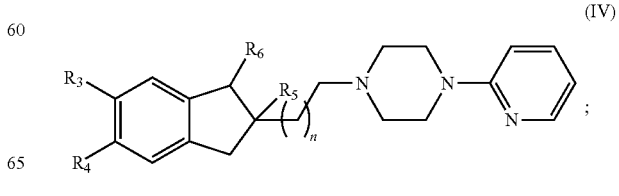

wherein X is C=O, CH$_2$, or O;
wherein R$_1$ is AcHN or NH$_2$;
wherein R$_2$ is H or =O;
wherein R$_3$ is Cl or H;
wherein R$_4$ is Cl, F, I, Br or H;
wherein R$_5$ is CH$_3$ or H;
wherein R$_6$ is =O, H or OH;
wherein n is an integer from 1 to 3; and
a pharmaceutically acceptable carrier.

The neurological disorder may be depression, anxiety, schizophrenia, or cognitive deficits caused by Alzheimer disease.

In an embodiment, the composition used to treat the neurological disorder may comprise a compound of Formula (IV), wherein R$_3$ is H, R$_4$ is Cl, R$_5$ is CH$_3$, R$_6$ is =O and n is 2.

BRIEF DESCRIPTION OF THE DRAWINGS

For a fuller understanding of the invention, reference should be made to the following detailed description, taken in connection with the accompanying drawings, in which:

FIG. 15 is a series of graphs depicting in vitro serotonin receptor, 5-HT$_{7A}$ adenylate cyclase functional assay results for compound 21. Graphs showing the specific cAMP formation for agonist activity of compound 21 in comparison to Serotonin (top graph) and antagonist activity of Compound 21 in comparison to Lurasidone (bottom graph).

DETAILED DESCRIPTION OF THE PREFERRED EMBODIMENT

Figure 1:
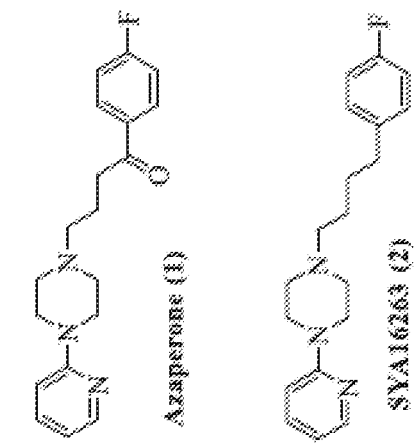
FIG. 1 is an image depicting structures of prior art FDA approved CNS drugs containing N-Aryl/heteroaryl piperazine moieties along with Azaperone (a) and SYA16263 (2).
Figure 1:
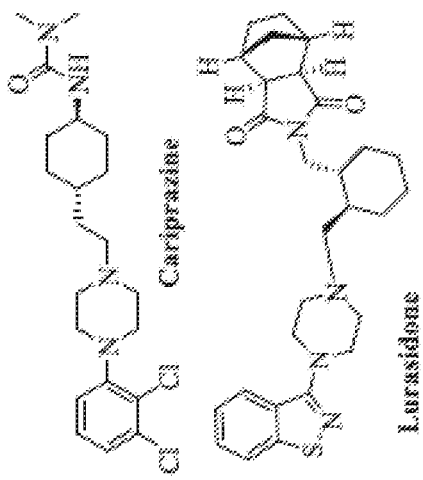
Figure 1:
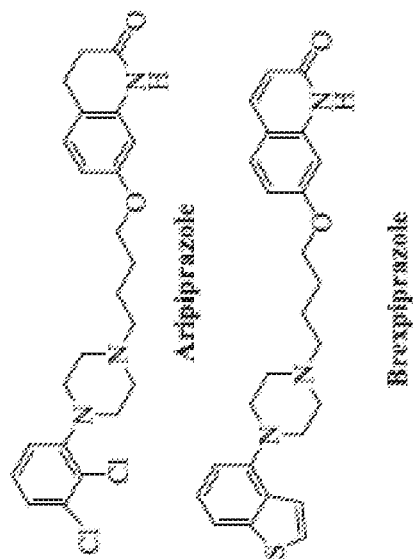

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

As used herein, the singular forms "a," "an" and "the" include plural referents unless the context clearly dictates otherwise.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about." It is also to be understood, even if it is not always explicitly stated, that the reagents described herein are merely exemplary and that equivalents of such are known in the art and can be substituted for the reagents explicitly stated herein.

As used herein, "about" means approximately or nearly and in the context of a numerical value or range set forth means±10% of the numerical.

As used herein, the term "comprising" is intended to mean that the products, compositions, and methods include the referenced components or steps, but not excluding others. "Consisting essentially of" when used to define products, compositions, and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein "patient" is used to describe an animal, preferably a human, to whom treatment is administered, including prophylactic treatment with the compositions of the present invention. "Patient" is used interchangeably with "subject" herein.

As used herein "animal" means a multicellular, eukaryotic organism classified in the kingdom Animalia or Metazoa. The term includes, but is not limited to, mammals. Non-limiting examples include rodents, mammals, aquatic mammals, domestic animals such as dogs and cats, farm animals such as sheep, pigs, cows and horses, and humans. Wherein the terms "animal" or the plural "animals" are used, it is contemplated that it also applies to any animals.

As used herein, the term "pharmaceutically acceptable carrier" is used to describe any of the standard pharmaceutically acceptable carriers. The pharmaceutically acceptable carrier can include excipients such as diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin EW [1995] Easton Pennsylvania, Mack Publishing Company, 19' ed.) describes formulations which can be used in connection with the subject invention.

Any of the compounds disclosed herein may be administered with or without an excipient. Excipients include, for example, encapsulating materials or additives such as absorption accelerators; antioxidants; binders; buffers; coating agents; coloring agents; diluents; disintegrating agents; emulsifiers; extenders; fillers; flavoring agents; humectants; lubricants; perfumes; preservatives; propellants; releasing agents; sterilizing agents; sweeteners; solubilizers; wetting agents; and mixtures thereof.

As used herein, "administering" or "administration" refers to the process by which the compounds of the present invention are delivered to a subject. The compounds of the present invention may be administered in a variety of ways including, but not limited to, bucally, orally, or parenterally (intramuscularly, intraperitoneally, intrasternally, intravenously, subcutaneously). Any of the compounds may also be delivered through encapsulation in vesicles such as liposomes, niosomes, micelles, etc.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. It is contemplated that one of ordinary skill in the art can determine and administer the appropriate dosage of compounds disclosed in the current invention according to the foregoing considerations.

Dosing frequency for the composition includes, but is not limited to, at least about once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months or longer. In some embodiments, there is no break in the dosing schedule. In some embodiments, the interval between each administration is no more than about a week.

The compounds used in the present invention may be administered individually, or in combination with or concurrently with one or more other compounds used to treat neurological disorders. Additionally, compounds used in the present invention may be administered in combination with or concurrently with other therapeutics for neurological disorders.

The term "compound" as used herein refers to a chemical formulation, either organic or inorganic, which induces a desired pharmacological and/or physiological effect on a subject when administered in a therapeutically effective amount. "Compound" is used interchangeably herein with "drug" and "therapeutic agent."

"Treatment" or "treating" as used herein refers to any of: the alleviation, amelioration, elimination and/or stabilization of a symptom or characteristic, as well as delay in progression of a symptom of a particular disorder. For example, "treatment" of a neurological disorder may include any one or more of the following: amelioration and/or elimination of one or more symptoms/characteristics associated with a neurological disorder, reduction of one or more symptoms/characteristics of a neurological disorder, stabilization of symptoms/characteristics of a neurological disorder, and delay in progression of one or more symptoms/characteristics of a neurological disorder.

"Neurological disorder" as used herein refers to a disorder or disease which affects the central or peripheral nervous system. Particularly, the compounds and compositions described herein bind to one or more serotonin receptors to provide antidepressant, antianxiety, and antipsychotic effects. In some embodiments, the compounds are dual $5\text{-HT}_{1A}$ and $5\text{-HT}_7$ receptor ligands capable of treating various CNS related conditions including cognitive and anxiolytic impairments Exemplary neurological disorders treated by the compounds and compositions of the instant invention include, but are not limited to, depression, anxiety, schizophrenia, and Alzheimer's disease.

As used herein, the term "therapeutically effective amount" is determined based on such considerations as known in the art including the recipient of the treatment, the recipient's tolerance for the compound, the disorder being treated, the severity of the disorder being treated, the composition containing the compound, the time of administration, the route of administration, the duration of treatment, the potency of the compound, the bioavailability of the compound, the rate of clearance of the compound from the body, and whether or not another active agent is co-administered. The amount of the compound of the instant invention that may be administered to a subject must be effective to achieve a response, including but not limited to, improved survival rate, more rapid recovery, and improvement or elimination of symptoms associated with neurological disorders. In accordance with the present invention, a suitable single dose size is a dose that is capable of preventing or alleviating (reducing or eliminating) a symptom in a patient when administered one or more times over a suitable time period. One of ordinary skill in the art can readily determine appropriate single dose sizes for systemic administration based on the size of a mammal and the route of administration.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms.

Chemistry

Azaperone (1) is a commercially available compound and the inventors previously reported SYA16263 (2) [27]. In general, the final compounds evaluated herein were obtained by refluxing or carrying out a microwave-assisted synthesis (MWAS) reaction of the amine portion, 1-(pyridin-2-yl) piperazine, with various alkylating agents in DME, $CH_3CN$ or toluene in the presence of $K_2CO3$ or $NaHCO_3$ as a base and a catalytic amount of KI. Final target compounds, where applicable, were converted to the HCl or oxalate salts. Comprehensive descriptions of the synthetic methods and accompanying data are provided in the experimental section.

Figure 2:
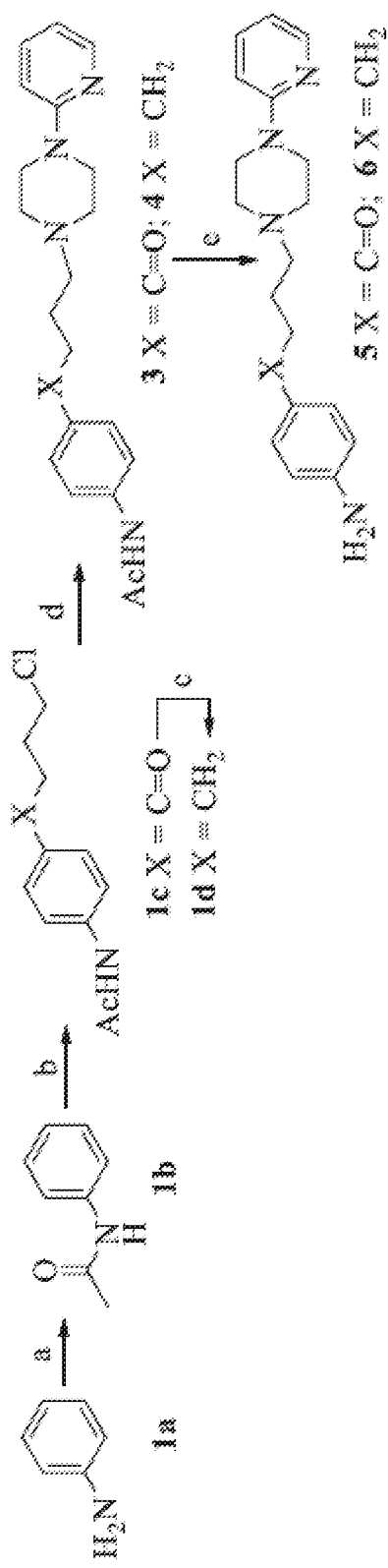
FIG. 2 is an image depicting Scheme 1 to synthesize compounds 3-6 disclosed herein. Reagents and conditions: (a) acetyl chloride, DCM, Et$_3$N; (b) 4-chlorobutyryl chloride, AlCl$_3$, CS$_2$, reflux; (c) triethylsilane (TES), TFA, 0° C.-rt, 15 min; (d) 1-(pyridine-2-yl)piperazine, K$_2$CO$_3$/KI, DME, MWAS; (e) conc. HCl/AcOH, MWAS, 30 min.

Briefly, in order to produce the alkylating agent 1c and 1d, aniline (1a) was N-acetylated under basic conditions and the resulting acetanilide (1b) acylated with 4-chlorobutyryl chloride under Friedel-Crafts conditions to produce intermediate 1c (Scheme 1). The keto group in 1c was removed under a modified phenyl-keto reduction reaction described by West and colleagues [30] to afford the intermediate 1d (Scheme 1). Alkylating agents 1c and 1d were then separately reacted with 1-(pyridin-2-yl)piperazine to produce acetamides 3 and 4, respectively. Deacetylation of 3 and 4 under acidic conditions following a modified method described by Kilbourn et al. [31] afforded 5 and 6 respectively (Scheme 1 shown in FIG. 2).

Figure 3:
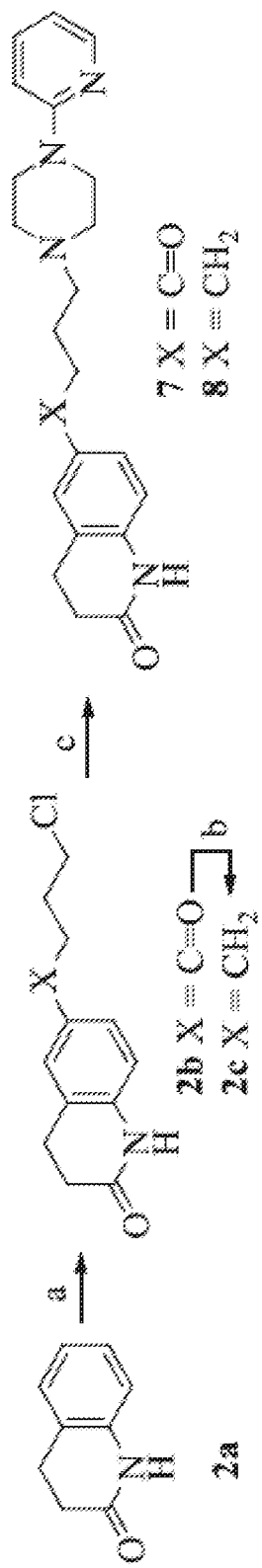
FIG. 3 is an image depicting Scheme 2 to synthesize compounds 7 and 8 disclosed herein. Reagents and conditions: (a) 4-chlorobutyryl chloride, AlCl$_3$, CS$_2$, reflux; (b) triethylsilane (TES), TFA, 0° C.-rt, 15 min; (c) 1-(pyridine-2-yl)piperazine, K$_2$CO$_3$/KI, DME, MWAS.

Compounds 7 and 8 were prepared by first acylating dihydrocarbostyril 2a under Friedel-Crafts acylation conditions as described in Scheme 1 to produce ketone 2b which was subsequently reduced, similar to 1c, to produce the alkyl halide 2c (Scheme 2). The alkyl halides 2b and 2c were separately reacted with 1-(pyridin-2-yl)piperazine leading to compounds 7 and 8 respectively (Scheme 2 shown in FIG. 3).

Figure 4:
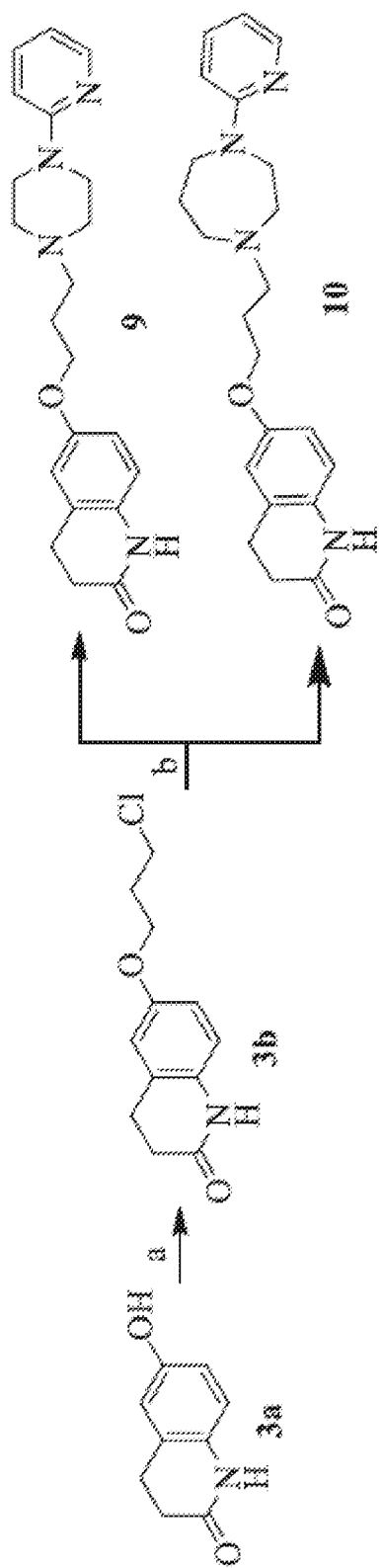
FIG. 4 is an image depicting Scheme 3 to synthesize compounds 9 and 10 disclosed herein.

Commercially available 6-hydroxy-dihydrocarbostyril 3a was O-alkylated with 1-bromo-3-chloropropane to give intermediate 3b which was then used to react separately with 1-(pyridin-2-yl)piperazine and 1-(pyridin-2-yl)-1,4-diazepane under the general alkylation procedure to produce compounds 9 and 10 respectively (Scheme 3 shown in FIG. 4).

Figure 5:
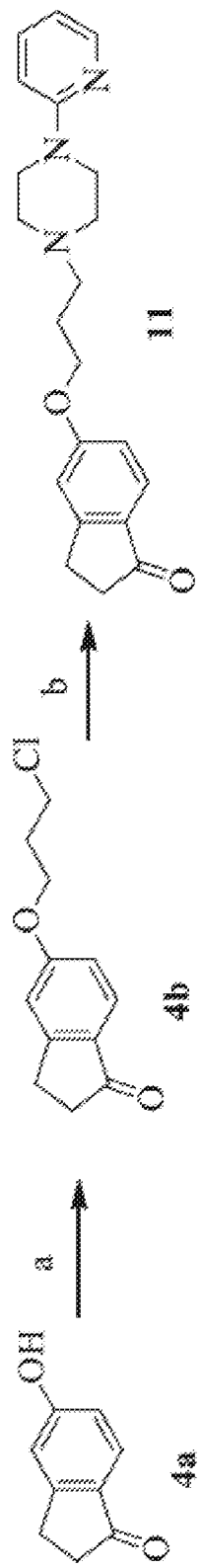
FIG. 5 is an image depicting Scheme 4 to synthesize compound 11 disclosed herein.

To access the alkylating agent 4b, 5-hydroxy-2,3-dihydro-1Hinden-1-one 4a was O-alkylated under similar condition as 3a (Scheme 3). The resulting alkylating agent was subsequently reacted with 1-(pyridin-2-yl)piperazine to afford compound 11 (Scheme 4 shown in FIG. 5).

Figure 6:
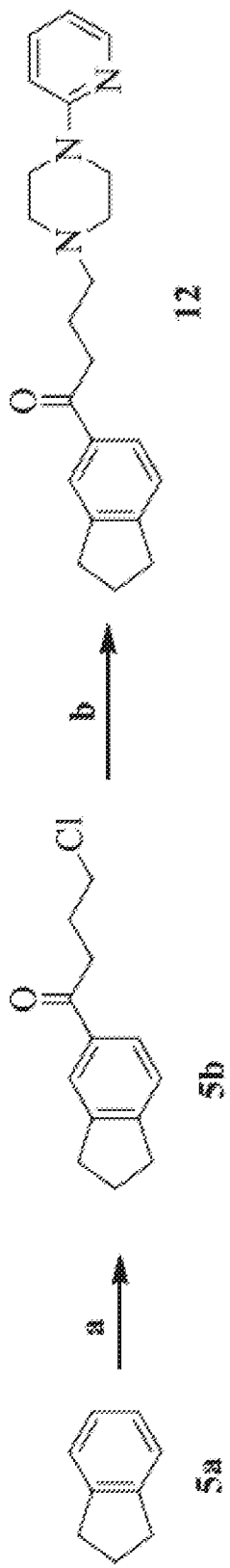
FIG. 6 is an image depicting Scheme 5 to synthesize compound 12 disclosed herein.

To prepare compound 12, the indane 5a was similarly acylated as 1c and 2b (Schemes 1 and 2) to produce the ketone 5b which was then used to react with 1-(pyridin-2-yl)piperazine under the general alkylation conditions to produce compound 12 (Scheme 5 shown in FIG. 6).

Figure 7:
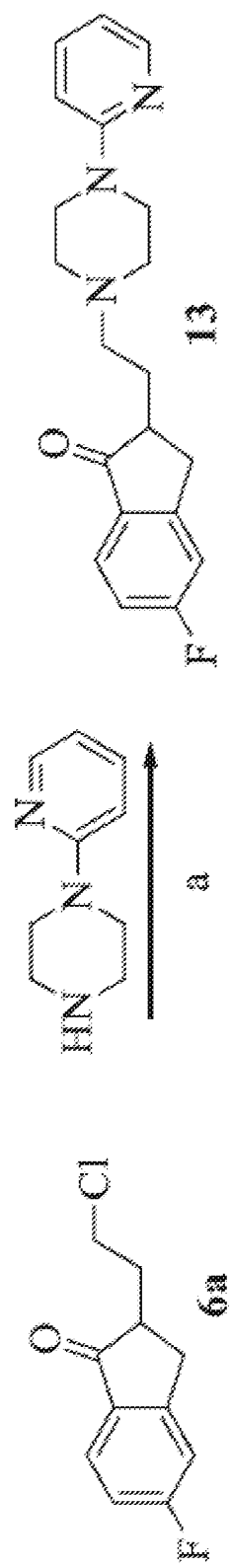
FIG. 7 is an image depicting Scheme 6 to synthesize compound 13 disclosed herein.

In order to obtain compound 13, the alkylating agent 5-chloro-2-(2-chloroethyl)-2,3-dihydro-1H-inden-1-one 6a previously reported by the inventors [27,32,33], was reacted with 1-pyridin-2-yl-piperazine under general alkylation reaction conditions (Scheme 6 shown in FIG. 7).

Figure 8:
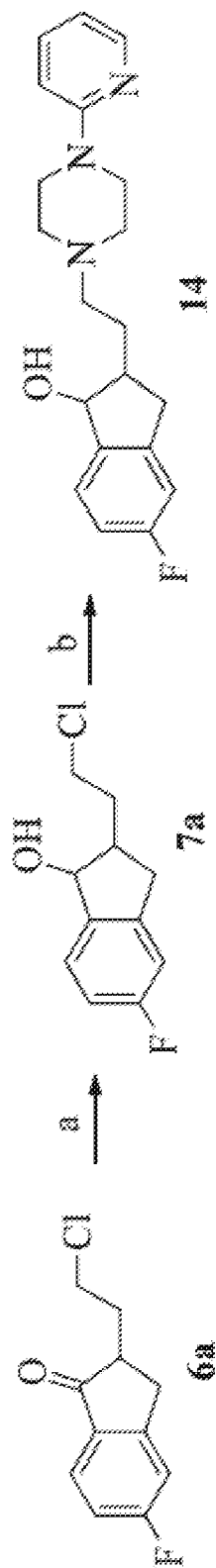
FIG. 8 is an image depicting Scheme 7 to synthesize compound 14 disclosed herein.

Ketone 6a was reduced under Luche reduction [34] conditions to yield alcohol 7a that was subsequently used to N-alkylate 1-pyridin-2-yl-piperazine to produce compound 14 (Scheme 7 shown in FIG. 8).

Figure 9:
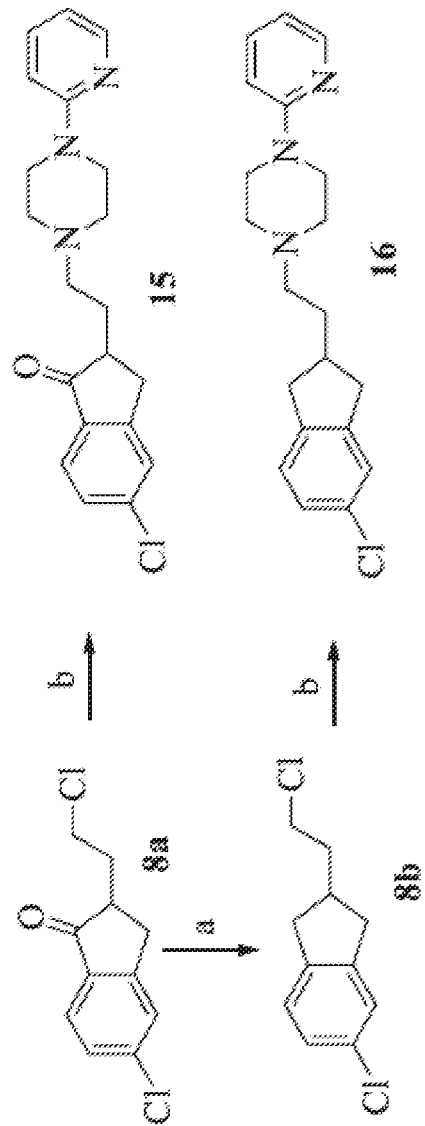
FIG. 9 is an image depicting Scheme 8 to synthesize compounds 15 and 16 disclosed herein.

Alkylating agent 8a, previously reported by the inventors [27,33], was reduced to produce indane 8b under Clemmensen reduction conditions. Under the general alkylation conditions, alkylating agents 8a and 8b were separately reacted with 1-pyridin-2-yl-piperazine to produce compounds 15 and 16 respectively (Scheme 8 shown in FIG. 9).

Figure 10:
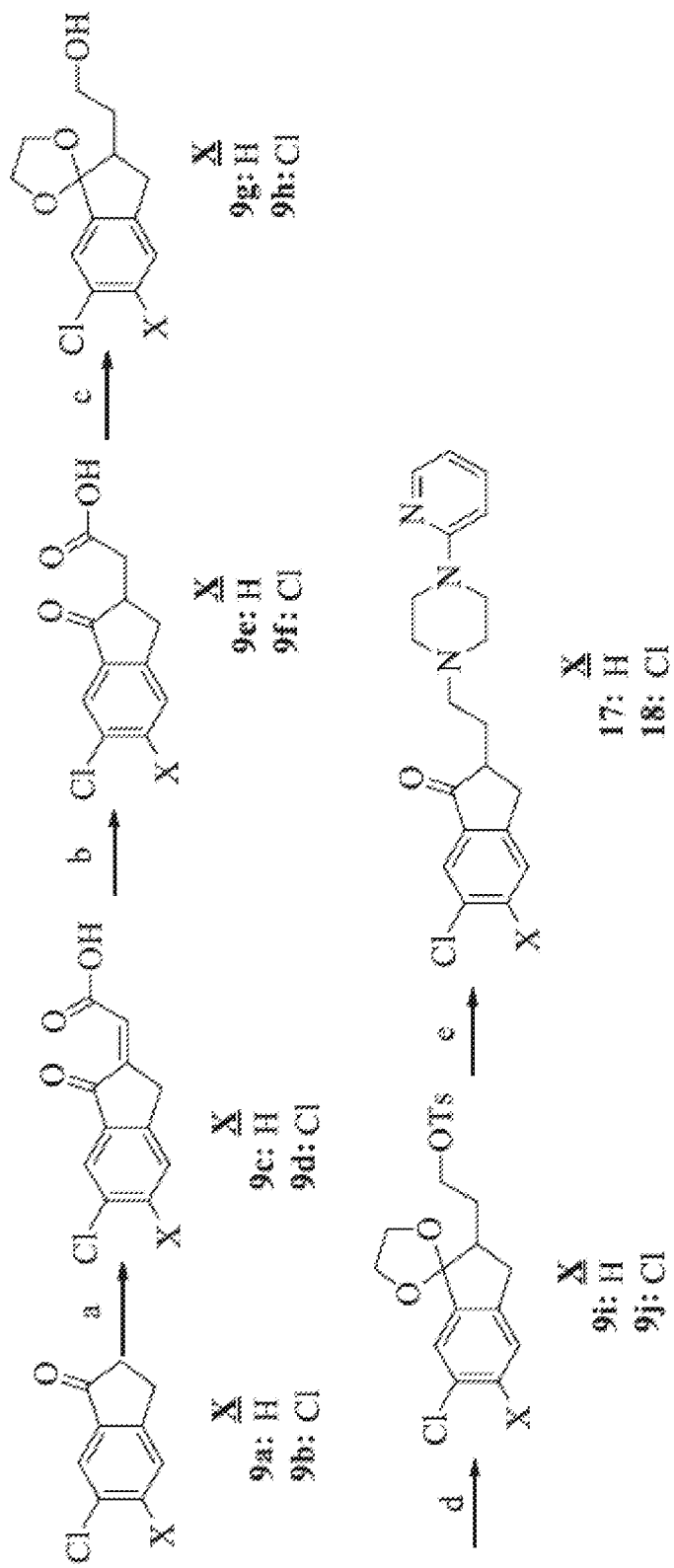
FIG. 10 is an image depicting Scheme 9 to synthesize compounds 17 and 18 disclosed herein.

To synthesize compounds 17 and 18, a five-step procedure (Scheme 9) similar to that reported by the inventors [32] was followed. Briefly, commercially available chloroindanones 9a and 9b were separately refluxed with glyoxylic acid in an aqueous sulfuric acid under a cross-aldol condensation reaction to afford the α,β-unsaturated ketones 9c and 9d, respectively. Next, the obtained ketones were reduced under the palladium-carbon catalyzed hydrogenation reaction to afford the 7-keto-carboxylic acids 9e and 9f, respectively. Ethylene ketal protection of the keto groups in each intermediate and subsequent reduction of the carboxylic function to an alcohol using $LiAlH_4$ produced the corresponding alcohols 9 g and 9 h. The alcohol functions were separately converted to the tosylate to form alkylating agents 9i and 9j respectively and were used to react with 1-pyridin-2-yl-piperazine followed by deprotection to make the final compounds 17 and 18 (Scheme 9 shown in FIG. 10) respectively.

Figure 11:
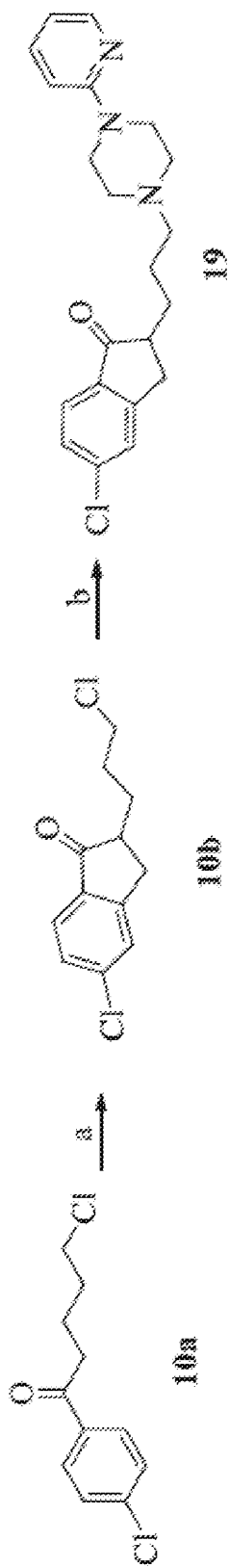
FIG. 11 is an image depicting Scheme 10 to synthesize compound 19 disclosed herein.

Synthesis of 5-chloro-1-(4-chlorophenyl)pentan-1-one 10a followed a similar procedure as reported by Komissarov et al. [35] and the resulting alkyl halide was subjected to the same two-step reaction reported by the inventors [27,33] to prepare the indanone 10b. Following same general alkylation procedure compound 19 was prepared in good yield (Scheme 10 shown in FIG. 11).

Figure 12:
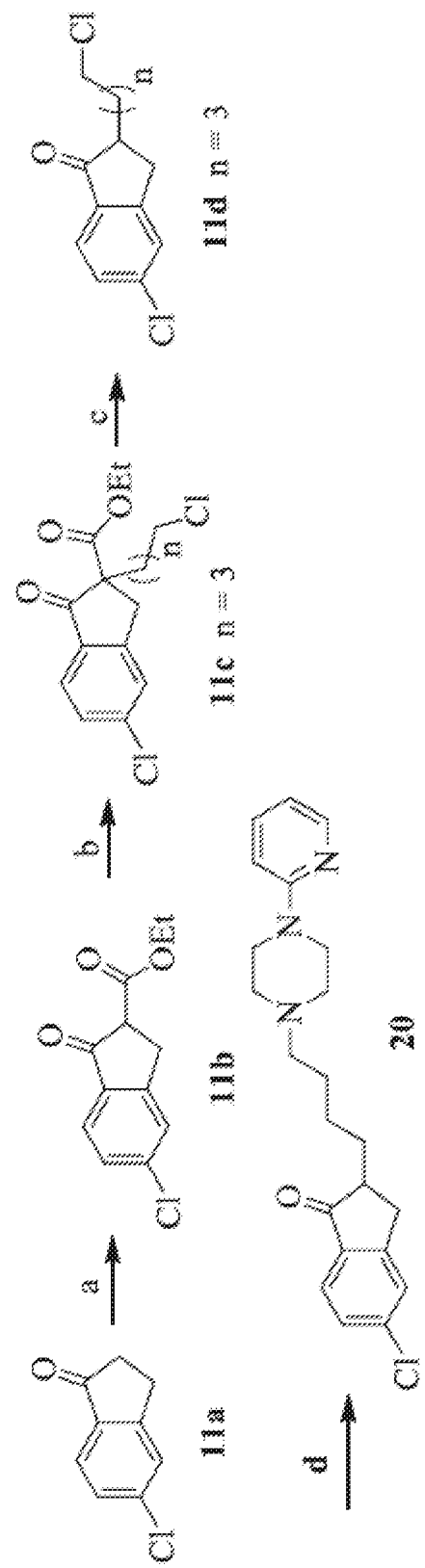
FIG. 12 is an image depicting Scheme 11 to synthesize compound 20 disclosed herein.

Claisen condensation of the 5-substituted-indanone 11a with diethylcarbonate (DEC) under basic conditions afforded the key 3-keto ester 11b. Subsequent alkylation of the β-keto ester with the 1-bromo-4-chlorobutane produced the C-disubstituted β-keto esters 11c. An acid catalyzed decarboxylation of 11c under microwave heating conditions produced the alkylating agent 11d in good to moderate yield (Scheme 11). This decarboxylation method was a variant of what was described by Ulrich, Jordis, and colleagues [36]. The obtained alkylating agent 11d was reacted with 1-pyridin-2-ylpiperazine under the general alkylation conditions to produce compound 20 (Scheme 11 shown in FIG. 12).

Figure 13:
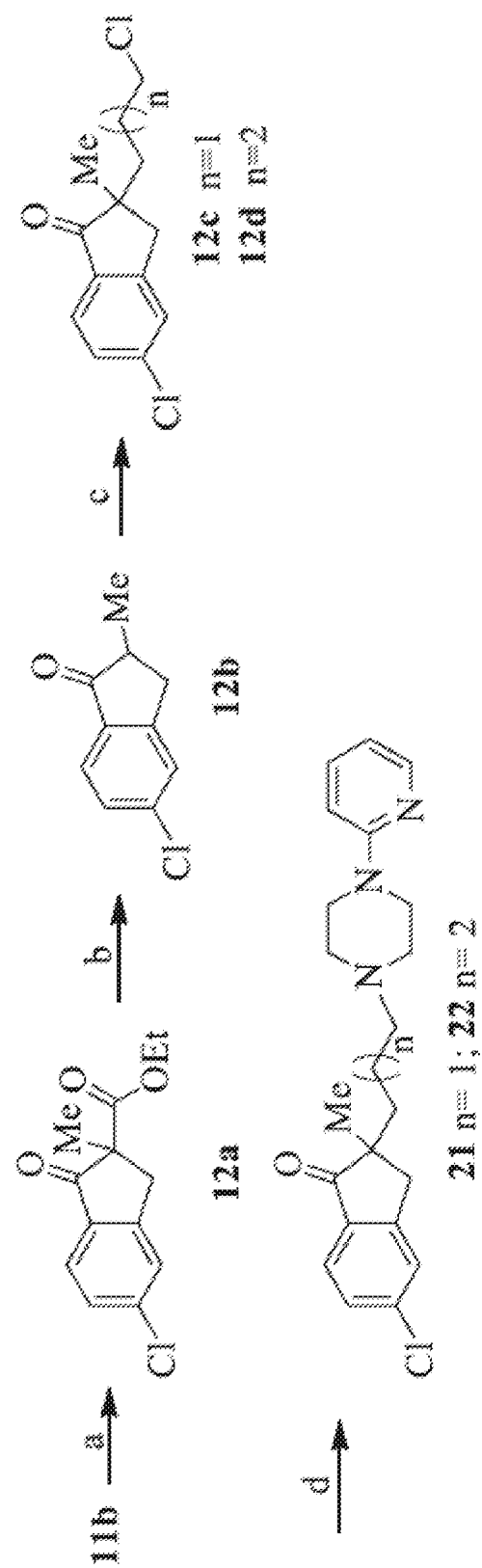
FIG. 13 is an image depicting Scheme 12 to synthesize compounds 21 and 22 disclosed herein.

To prepare the α-methylated 5-chloroindanone 12b, the β-keto ester 11a obtained from Scheme 11 was deprotonated and methylated under basic conditions to produce intermediate 12a (Scheme 12 shown in FIG. 13) which was decarboxylated to yield 12b. The alkylation step was repeated using 1-bromo-3-chloropropane and 1-bromo-4-chlorobutane to produce alkylating agents 12c and 12d respectively which were reacted separately with 1-(pyridin-2-yl)piperazine to afford compounds 21 and 22, respectively.

Results and Discussion

The previous campaign expanded the antipsychotic potential of butyrophenones, and the inventors reported that 1-(4-(4-fluorophenyl)butyl)-4-(pyridin-2-yl)piperazine (SYA16263 (2)) displays desirable multi-receptor binding affinity for D2-like receptors (Ki:$D_2$=124 nM, $D_3$=86 nM, $D_4$=3.5 nM), and 5-HTRs (Ki: 5-$HT_{2A}$, =50 nM, 5-$HT_7$=90 nM), particularly the 5-$HT_{1A}$ receptor (Ki 5-$HT_{1A}$=1.1 nM), (Table 1). Previous functional and in vivo behavioral studies indicated that compound 2 is a β-arrestin biased ligand at D2R and has low propensity to cause catalepsy in rats, a key early test to screen antipsychotic agents with the potential to cause motoric side effects [29]. Inspired by these seminal results, the inventors embarked on SAFIR studies to explore the effects of structural changes in compound 2 on binding affinity at key CNS receptors. Due to the metabolic side effects associated with ligands that interact with 5-HT2CR, all compounds were evaluated for binding affinity at this receptor.

To probe the effects of electronic features of the para position of the phenyl ring in compounds 1 and 2, the inventors introduced acetanilide (—NHC(O)CH$_3$) and amino (—NH$_2$) groups to produce compounds β-6 and the binding affinity constants are reported in Table 1. Generally, these compounds showed no improvement in affinity for the clinically relevant DA and 5-HT receptors, compared to SYA16263. In particular, these changes were not tolerated at the $D_4$ receptor. However, these compounds maintained moderate binding affinity at 5-$HT_{1A}$, 5-$HT_{2A}$ and 5-HT7 receptors.

Replacing the p-fluoro-phenyl group in azaperone 1 with dihydrocarbostyril moiety to form compound 7 led to a 25-fold increase in binding affinity at the 5-$HT_7R$ (Ki=4.8 nM), moderate binding affinity at 5-$HT_{1A}R$ (Ki=47.3 nM) and loss of activity at $D_2R$. Deoxygenating the keto function in compound 7 to obtain 8 restored the high binding potency at 5-$HT_{1A}R$ (Ki=4.5 nM) with moderate to low affinity at all other receptors as reported in Table 1. Replacing the benzylic carbon at position 6 of the dihydrocarbostyril moiety found in 8 with an oxygen atom to give compound 9 did not produce any significant improvement in binding affinity at all receptors evaluated. Similarly, expanding the piperazine ring in compound 9 to a homopiperazine in 10 resulted in diminished affinity for all receptors under consideration, especially at 5-$HT_{1A}R$ where there was a 20-fold decrease in potency compared to compound 9 (9: Ki (5-$HT_{1A}$)=20.3 nM vs 10: Ki (5-$HT_{1A}R$)=411 nM) (Table 1). This suggests that the six-membered piperazine ring is essential for maintaining activity at 5-$HT_{1A}R$. Removing the anilino-nitrogen in the dihydrocarbostyril moiety in 9 gave 11, which displayed no apparent improvement in affinity across all evaluated receptors. Further modification by replacing p-fluoro-phenyl in azaperone with dihydro-indene to obtain compound 12 restored the high binding affinity at 5-$HT_{1A}R$ (Ki=5.2 nM) and D4R (Ki=14 nM) while binding affinity for other receptors was either moderate or diminished.

TABLE 1

Binding affinity constants[a] [mean Ki, nM & (pKi ± SEM)[b,c]] at relevant CNS receptors and SERT transporter

| Compound | $D_2$ | $D_3$ | $D_4$ | 5-$HT_{1A}$ | 5-$HT_{2A}$ | 5-$HT_{2C}$ |
|---|---|---|---|---|---|---|
| 1 Azaperone | 228 (6.64 ± 0.06) | 89.7 (7.12 ± 0.09) | 6.7 (8.2 ± 0.07) | 8.1 (8.12 ± 0.05) | 62.7 (7.34 ± 0.06) | 1,540.3 (5.87 ± 0.07) |
| 2 (SYA16263)[d] | 124 ± 110 | 86 ± 4 | 3.5 ± 0.2 | 1.1 ± 0.05 | 50 ± 3 | MT |
| 3 | 1092 (5.96 ± 0.07) | 218 (6.66 ± 0.05) | 2384 (5.62 ± 0.04) | 93 (7.03 ± 10.07) | 108 (6.97 ± 10.04) | 244 (6.61 ± 0.07) |
| 4 | 1930 (5.71 ± 0.08) | 203 (6.69 ± 10.05) | >10000 (<5) | 14 (7.84 ± 0.06) | 384.5 (6.45 ± 10.05) | 242 (6.62 ± 0.07) |
| 5 | 1095 (5.96 ± 0.07) | 469 (6.33 ± 10.05) | 577 (6.24 ± 0.03) | 27 7.57 ± 0.07 | 176.5 (6.81 ± 0.05) | 35 (7.5 ± 0.1) |
| 6 | 674 (6.17 ± 0.08) | 391 (6.41 ± 0.05) | 1872 (5.73 ± 0.03) | 13 (7.87 ± 0.06) | 626 (6.2 ± 0.04) | MT |

TABLE 1-continued

| # | Structure | | | | | | |
|---|---|---|---|---|---|---|---|
| 7 | 3,4-dihydroquinolin-2(1H)-one-6-yl butanone-piperazine-pyridine | >10,000 (<5) | 382.5 (6.4 ± 0.07) | 471 (6.39 ± 0.05) | 47.3 (7.3 ± 0.08) | 3111 (5.5 ± 0.06) | MT |
| 8 | 3,4-dihydroquinolin-2(1H)-one-6-yl butyl-piperazine-pyridine | 526.5 (6.3 ± 0.1) | 205.5 (6.69 ± 0.08) | 146.3 (6.87 ±1 0.09) | 4.5 (8.39 ± 0.07) | 564.3 (6.27 ± 0.05) | 1,130 (5.95 ± 0.06) |
| 9 | 3,4-dihydroquinolin-2(1H)-one-6-yloxy propyl-piperazine-pyridine | 2,667 (5.57 ± 0.08) | 647.5 (6.23 ± 0.05) | 496 (6.3 ± 10.05) | 20.3 (7.72 ± 0.08) | 318.3 (6.54 ± 0.07) | 1,192 (5.92 ± 0.07) |
| 10 | 3,4-dihydroquinolin-2(1H)-one-6-yloxy propyl-homopiperazine-pyridine | 2,798 (5.55 ± 0.08) | 2,098 (5.68 ± 0.05) | MT | 411 (6.39 ± 0.06) | 1,132 (5.95 ± 0.07) | 6,662 (5.18 ± 10.08) |
| 11 | indanone-yloxy propyl-piperazine-pyridine | MT | 286 (6.54 ± 0.05) | 121 (6.92 ± 10.07) | 19 (7.72 ± 0.07) | 161 (6.79 ± 0.05) | 1005 (6 ± 0.06) |
| 12 | indanyl butanone-piperazine-pyridine | 699 (6.16 ± 0.07) | 376 (6.43 ± 0.05) | 14 (7.86 ± 0.05) | 5.2 (8.28 ± 0.06) | 345 (6.46 ± 0.05) | 111 (6.95 ± 0.09) |

Binding affinity constants[a] [mean Ki, nM & (pKi ± SEM)[b,c]] at relevant CNS receptors and SERT transporter

| | | 5-HT$_7$ | SERT |
|---|---|---|---|
| 1 Azaperone | | 120.5 (6.94 ± 0.08) | MT[b] |
| 2 (SYA16263)[d] | | 90 ± 4 | MT |
| 3 | 4-acetamidophenyl butanone-piperazine-pyridine | 420 6.38 ± 0.06 | MT |

TABLE 1-continued

| Structure | Affinity 1 | Affinity 2 |
|---|---|---|
| Compound 4 | 134 (6.87 ± 0.05) | MT |
| Compound 5 | 273 (6.56 ± 0.05) | MT |
| Compound 6 | 222 (6.65 ± 0.06) | MT |
| Compound 7 | 4.8 (8.32 ± 0.05) | MT |
| Compound 8 | 24.5 (7.64 ± 0.05) | 1,143 (5.96 ± 0.1) |
| Compound 9 | 187.5 (6.73 ± 0.05) | 3,064.6 (5.58 ± 0.1) |
| Compound 10 | 957 (6.02 ± 0.06) | 248 (6.61 ± 0.09) |
| Compound 11 | 1598 (5.85 ± 0.1) | MT |
| Compound 12 | 77 (7.12 ± 0.05) | MT |

[a]Results from NIMH PDSP; 5 MT = missed 50% threshold inhibition at 10 μM concentration;
[c]Data points without standard error (SE) have errors below 20% of the mean value.
[d]Previously reported in references 26, 28 and 29.

To further explore the SAR of the lead compounds (1 and 2), the inventors synthesized partially restrained butyl spacer analogs 13-18, and their binding affinity constants are reported in Table 2. Restraining the keto group in azaperone (1) into an indanone to produce 13 resulted in complete loss of binding affinity at $D_2R$. However, the inventors observed a 20-fold improvement in binding affinity at the 5-HT$_7$R (1: Ki=120.5 nM vs 13: Ki=11.91 nM) for 13, with no significant change in activity at other 5-HTRs. Reduction of the keto group in 13 to produce alcohol 14 and led to restoration of moderate binding affinity for the D$_2$R (Ki=510 nM) while maintaining a similar trend, but with reduced affinity, at other receptors in comparison to SYA16263 (2). Compounds 15 and 16, chloro-indanone analogs of 1 and 2 respectively, were synthesized to explore the effects of isosteric replacement of the fluoro atom with a chloro atom. Interestingly, 15 displayed significant selectivity for the D$_4$R (Ki=65 nM) as affinities at D$_2$R and D$_3$R were lost while maintaining moderate binding activity at other 5-HTRs (Table 2). Compound 16 displayed high binding affinity for 5-HT$_{1A}$R (Ki=6.1 nM) and moderate affinity for 5-HT$_7$R (Ki=45 nM). Moving the chloro atom (para to the keto group) in compound 15 to position 6 (meta to the keto group) of the indanone moiety produced 17, which resulted in little or no improvement in binding affinity at the 5-HTRs (except at 5-HT$_{1A}$ where it displayed high affinity (Ki=5.1 nM)) with no apparent gain in binding affinity for the D$_2$R. Further, the inventors introduced an additional chloro group into 15 to obtain compound 18 which can be viewed as a merge of 15 and 17. Again, this resulted in no significant gain in affinity at either DA or 5-HT receptors (Table 2).

TABLE 2

Binding affinity Constants$^a$ [mean Ki, nM & (pKi +SEM)$^{b,c}$] at relevant CNS receptors and SERT transporter

| Compound | D$_2$ | D$_3$ | D$_4$ | 5-HT$_{1A}$ | 5-HT$_{2A}$ | 5-HT$_{2C}$ |
|---|---|---|---|---|---|---|
| 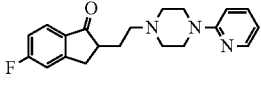<br>13 | MT$^b$ | 1469.8 | 41.39 | 11.39 | 75.09 | MT |
| 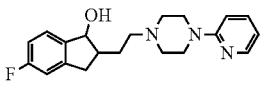<br>14 | 510 ± 37 | 347 ± 24 | 7.9 ± 0.5 | 8 ± 0.5 | 580 ± 37 | MT |
| 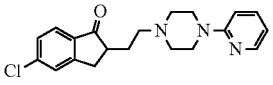 [SMILES: O=C1c2ccc(Cl)cc2CC1CCN1CCN(c2ccccn2)CC1]<br>15 | MT | MT | 65 (7.19 ± 0.08) | 32 (7.5 ± 0.09) | 113 (6.95 ± 0.04) | 1,980 (5.7 ± 0.05) |
| 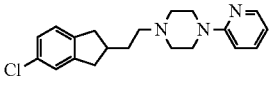 [SMILES: Clc1ccc2c(c1)CC(CCN1CCN(c3ccccn3)CC1)C2]<br>16 | 1,234 (5.91 ± 0.07) | 247 (6.61 ± 0.09) | 44 (7.36 ±1 0.06) | 6.1 (8.21 ± 0.07) | 110 (6.96 ± 0.04) | 2,729 (5.56 ± 0.08) |
| 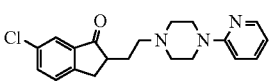<br>17 | 4,513 (5.35 ± 0.06) | 407 (6.39 ± 0.04) | 10 (7.99 ± 0.05) | 5.1 (8.3 ± 0.04) | 122 (6.91 ± 0.09) | 1,680 (5.77 ± 0.06) |
| 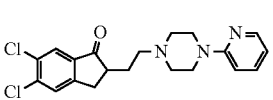 [SMILES: O=C1c2cc(Cl)c(Cl)cc2CC1CCN1CCN(c2ccccn2)CC1]<br>18 | 3,071 (5.51 ± 0.06) | 707 | 45.5 (7.35 ± 0.06) | 46 (7.33 ± 0.04) | 159 (6.8 ± 0.09) | 1,644 (5.78 ± 0.06) |

Binding affinity Constants$^a$ [mean Ki, nM & (pKi +SEM)$^{b,c}$] at relevant CNS receptors and SERT transporter

| Compound | 5-HT$_7$ | SERT |
|---|---|---|
| 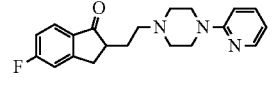<br>13 | 11.91 | MT |
| 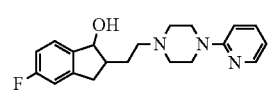<br>14 | 62 ± 3 | 392 ± 33 |

TABLE 2-continued

| | | | |
|---|---|---|---|
| 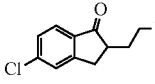 15 | 14 (7.84 ± 0.06) | MT | |
| 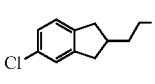 16 | 45 (7.34 ± 0.05) | MT | |
| 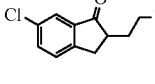 17 | 63 (7.2 ± 0.06) | MT | |
| 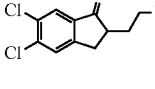 18 | 23 (7.64 ± 0.06) | MT | |

[a]Results from NIMH PDSP;
[b]MT = missed 50% threshold inhibition at 10 μM concentration;
[c]Data points without standard error (SE) have errors below 20% of the mean value.

Inspired by the interesting binding affinity profile of the chloroindanones in Table 2, and using 15 as the new lead compound, the inventors further explored the effect of chain length between the indanone moiety and the pyridinyl-piperazine group on binding affinity. To this end, the inventors synthesized compounds 19-22 and their binding affinities are reported in Table 3 of FIG. 16. Increasing the chain length from two (ethylenes) in 15 to three (propylenes) in 19 produced the much desired dual 5-$HT_{1A}$ and 5-$HT_7$ ligands with low nanomolar binding affinity constants (19: Ki (5-$HT_{1A}$R)=2.3 nM, Ki (5-$HT_7$R)=7.8 nM). Further elongation of the chain length to four in compound 20 resulted in a similar binding affinity profile as observed with 19, particularly at the 5-$HT_{1A}$R and 5-$HT_7$R targets. Next, the inventors explored the effects of introducing a methyl ($CH_3$) group at the alpha (α)-position of the indanone segment to replace the labile α-hydrogen in 19 and 20 to obtain compounds 21 and 22, respectively. In addition, this modification served as a perfect handle to mitigate keto-enol tautomerism that occurs in indanones, as reported by the inventors previously [37]. Interestingly, 5-chloro-2-methyl-2-(3-(4-(pyridin-2-yl) piperazin-1-yl)propyl)-2,3-dihydro-1H-inden-1-one (21) produced the highest affinity ligand at 5-$HT_{1A}$R (Ki=0.74 nM) and 5-$HT_7$R (Ki=8.4 nM) among the indanone-pyridinylpiperazine series. Taken together, the indanones identified herein tend to have poor affinity for $D_2$R, varying binding affinity for $D_3$R, moderate for $D_4$R (10 nM<Ki<100 nM) and moderate to high affinity at 5-$HT_{1A}$R, 5-$HT_{2A}$R, and 5-$HT_7$R. In fact, compound 21 has a higher affinity at the 5-$HT_{1A}$R and 5-$HT_7$R (Ki: =0.74 and 8.4 nM respectively) compared to aripiprazole (Ki: 5-$HT_{1A}$R and 5-$HT_7$R=5.6 and 10.3 nM respectively) [38].

TABLE 3

Binding affinities[a] [mean Ki, nM & (pKi ± SEM)[b,c]] at relevant CNS receptors and transporters

| Compound | $D_2$ | $D_3$ | $D_4$ | 5-$HT_{1A}$ | 5-$HT_{2A}$ |
|---|---|---|---|---|---|
| 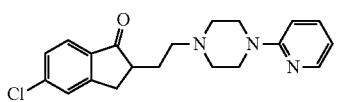 [SMILES: O=C1c2ccc(Cl)cc2CC1CCN1CCN(c2ccccn2)CC1] 15 | MT[b] | MT | 65 (7.19 ± 0.08) | 32 (7.5 ± 0.09) | 113 (6.95 ± 0.04) |
| 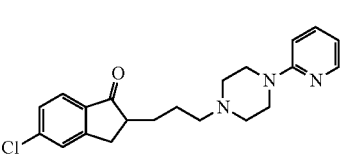 [SMILES: O=C1c2ccc(Cl)cc2CC1CCCN1CCN(c2ccccn2)CC1] 19 | MT | 80 (7.1 ± 0.09) | 31 (7.51 ± 10.04) | 2.3 (8.63 ± 0.08) | 533 (6.27 ± 0.05) |

TABLE 3-continued
| Structure | | | | | |
|---|---|---|---|---|---|
| 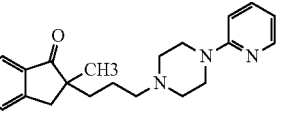<br>20 | 1,056<br>(5.98 ± 0.08) | 1,167.5<br>(6.01 ± 0.06) | 64<br>(7.19 ± 0.05) | 4.4<br>(8.39 ± 0.08) | 440.3<br>(6.4 ± 0.07) |
| 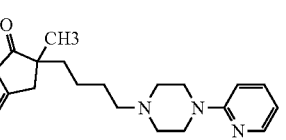<br>21 | 1096<br>(5.96 ± 0.05) | >10,000<br>(<5) | 48<br>(7.32 ± 0.09) | 0.74<br>(9.13 ± 0.08) | 200<br>(6.7 ± 0.07) |
| 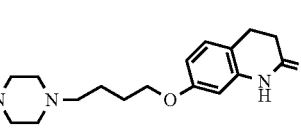<br>22 | 3260<br>(5.49 ± 0.09) | >10,000<br>(<5) | 143<br>(6.8 ± 0.1) | 2.45<br>(8.62 ± 0.09) | 578<br>(6.24 ± 0.07) |
| 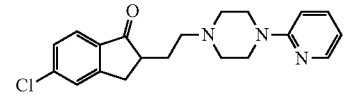 [SMILES: O=C1c2ccc(Cl)cc2CC1CCN1CCN(c2ccccn2)CC1]<br>[d]Aripiprazole | 3.3 ± 0.1 | 9.7 ± 5.4 | 510 ± 93 | 5.6 ± 0.8 | 8.7 ± 2.0 |
| Compound | 5-HT$_{2C}$ | 5-HT$_7$ | SERT |
|---|---|---|---|
| 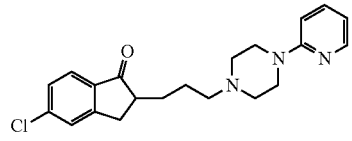 [SMILES: O=C1c2ccc(Cl)cc2CC1CCCN1CCN(c2ccccn2)CC1] | 1,980<br>(5.7 ± 0.05) | 14<br>(7.84 ± 0.06) | MT |
| 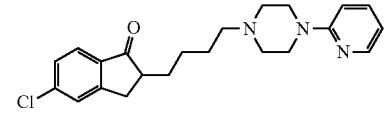 [SMILES: O=C1c2ccc(Cl)cc2CC1CCCCN1CCN(c2ccccn2)CC1] | 1875<br>(5.73 ± 0.04) | 7.8<br>(8.11 ± 0.06) | MT |
| 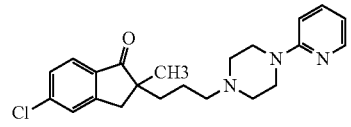 [SMILES: CC1(CCCN2CCN(c3ccccn3)CC2)Cc2cc(Cl)ccc2C1=O] | 367<br>(6.44 ± 0.07) | 15<br>(7.83 ± 0.05) | 2184<br>(5.72 ± 0.1) |
| 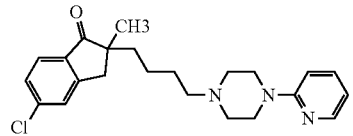 [SMILES: CC1(CCCCN2CCN(c3ccccn3)CC2)Cc2cc(Cl)ccc2C1=O] | 1448<br>(5.84 ± 0.07) | 8.4<br>(8.07 ± 0.08) | >10,000<br>(<5) |
|  | 1100<br>(5.96 ± 0.07) | 15<br>(7.82 ± 0.08) | >10,000<br>(<5) |

TABLE 3-continued

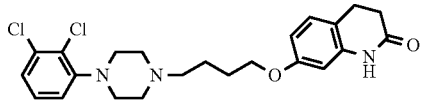 [SMILES: O=C1CCc2ccc(OCCCCN3CCN(c4cccc(Cl)c4Cl)CC3)cc2N1]

| Compound | | | |
|---|---|---|---|
| Aripiprazole[d] | 180 ± 37 | 10.3 ± 3.7 | 1080 ± 180 |

[a]Results from NIMH PDSP;
[b]MT = missed 50% threshold inhibition at 10 μM concentration.
[c]Data points without standard error (SE) have errors below 20% of the mean value.
[d]Aripiprazole data was obtained from reference 43.

The target compounds herein were also evaluated at the 5-HT2cR and the serotonin transporter (SERT). Overall, compounds reported herein displayed little if any affinity for SERT while no definitive trend was observed at the 5-HT2cR, with most of the target compounds showing poor to moderate binding affinities, particularly among the indanones.

Figure 14:
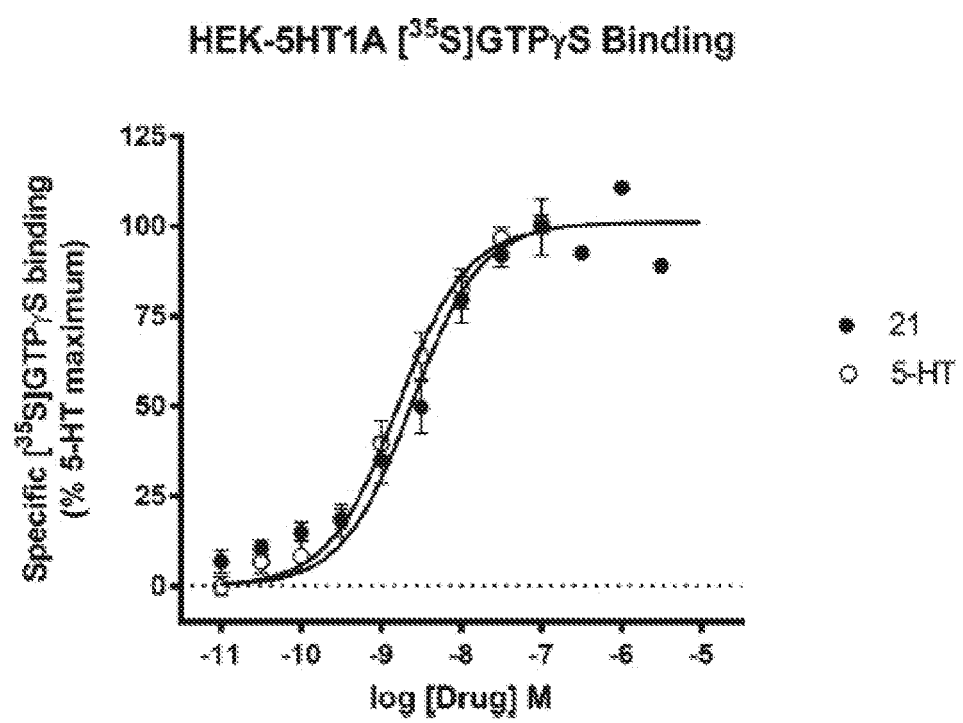
FIG. 14 is a graph depicting in vitro serotonin receptor HEK-5-HT$_{1A}$ [$^{35}$S]GTPγS binding functional assay results showing the agonistic activity for Compound 21 in comparison with serotonin.

The functional characteristics of compound 21, the highest dual affinity ligand identified in this study were assessed at the 5-HT$_{1A}$R and 5-HT$_{7A}$R (Table 4 and 5, FIGS. 14 and 15). As an agonist, serotonin has an EC$_{50}$ of 2.03 nM (% Max=101.5), whereas compound 21 has an EC$_{50}$ of 2.74 nM and is fully efficacious (% Max=100.5) (Table 4 & FIG. 14). As expected, serotonin similarly showed agonist properties at the 5-HT7AR but compound 21 did not display any agonist activity (Table 4 & FIG. 15). Looking at compound 21 in the antagonist assay, it had an IC$_{50}$ value of 100 nM and 101.5% inhibition of adenylate cyclase compared to lurasidone's IC$_{50}$ value of 15.72 nM and 100.0% adenylate cyclase inhibition (Table 5 & FIG. 15). Thus, compound 21 acts as a full agonist at the 5-HT$_{1A}$R but acts as an antagonist at the 5-HT$_{7A}$R. This functional characteristic is consistent with characteristics for treating cognitive impairments and for developing antidepressant drugs.

TABLE 4

Serotonin receptors functional assays, agonist effects

| | 5-HT$_{1A}$R GTPγS binding | | | | | 5-HT$_{7A}$R adenylate cyclase | | | | |
|---|---|---|---|---|---|---|---|---|---|---|
| Compound | EC$_{50}$ | SEM | n | % max | SEM | EC$_{50}$ | SEM | n | % 5-HT | SEM |
| 21 | 2.74 | 0.91 | 4 | 100.5 | 3.6 | >10 μM | | 1 | 0 | |
| Serotonin | 2.03 | 0.56 | 6 | 101.5 | 1.5 | 3.66 | 0.52 | 2 | 96.9 | 1.9 |

TABLE 5

Serotonin receptors functional assays, antagonist effects

| | 5-HT$_{1A}$R GTPγS binding | | | | | 5-HT$_{7A}$R adenylate cyclase | | | | |
|---|---|---|---|---|---|---|---|---|---|---|
| Compound | IC$_{50}$ | SEM | n | % max inhibition | SEM | IC$_{50}$ | SEM | n | % max inhibition | SEM |
| 21 | — | | | | | 100 | 14 | 2 | 101.5 | 0.1 |
| Lurasidone | | | | | | 15.72 | 0.26 | 2 | 100.0 | 0.0 |

In conclusion, using SYA16263 (2), which displayed high selectivity (>80 fold) for 5-HT$_{1A}$R compared to 5-HT$_7$R as the lead molecule, the inventors have now identified very high affinity dual acting ligands for 5-HT$_{1A}$ and 5-HT$_7$ receptors. Notably, the chloroindanone pyridinyl-piperazine compound, 21 showed sub-nanomolar and low nanomolar binding affinities at the 5-HT$_{1A}$R and 5-HT$_7$R and with full agonist and antagonist effects at the respective receptors. Compound 21 is thus a valuable addition to the rather scarce group of reported dual 5-HT$_{1A}$R and 5-HT$_7$R selective ligands. It is anticipated that 21 may serve as a chemical probe for further exploitation of the SAR of multi-target ligands for CNS drug discovery.

Materials and Methods

Chemistry

Melting points were determined on a Gallenkamp (UK) apparatus and are uncorrected. All NMR spectra were obtained on a Varian 300 MHz Mercury Spectrometer and the free induction decay (FID) data were processed using Mestrelab's Mnova NMR software (version 8.1) to obtain the reported NMR data. Elemental analyses were carried out by Atlantic Microlab, Inc., Norcross, GA, and are within 0.4% of theory unless otherwise noted. Flash chromatography was performed using a Teledyne CombiFlash® with Davisil grade 634 silica gel. Starting materials were obtained from Sigma-Aldrich and were used without further purification. All microwave assisted syntheses (MWAS) were carried out using a Biotage Initiator®.

Acetanilide (1b)

Acetanilide 1b was prepared by acetylating aniline following a simple method described by Zhang and co-workers [39]. Briefly, to a mixture of aniline (3.7 mL, 40 mmol) and triethylamine (7.3 mL) in dry $CH_2Cl_2$ (50 mL) was added acetyl chloride (3.2 mL, 44 mmol) dropwise while stirring. After addition, the mixture was allowed to stir for 4 h at room temperature. The reaction was quenched by adding water (20 mL) and the organic layer washed further with water (2×20 mL), brine (50 mL), dried using $Na_2SO_4$ and concentrated in-vacuo to obtain acetanilide (5 g, 93%) as solid needle-like crystals. 1H NMR (300 MHz, $CDCl_3$) d 8.77 (1H, s), 7.59-7.48 (2H, m), 7.33-7.20 (2H, m), 7.13-7.01 (1H, m), 2.12 (3H, s). 13C NMR (75 MHz, $CDCl_3$) d 169.50, 138.22, 128.83, 124.25, 120.38, 24.29.

N-(4-(4-chlorobutanoyl)phenyl)acetamide (1c)

A modified acylation reaction described by Lackey et al. [40] was followed to access intermediate 1c. Briefly, to a dry 100 mL round-bottomed flask equipped with a stirrer was added $AlCl_3$ (5 g, 37.5 mmol) carbon disulfide ($CS_2$) (30 mL) and 4-chlorobutyryl chloride (2.5 mL, 22.5 mmol) at 0° C. with stirring. To the mixture obtained was added 1b (15 mmol) portion-wise over 20 min. After addition is complete, the reaction mixture was allowed to warm to room temperature and stirred overnight. The content was dumped into a beaker containing 100 g of ice with 5 mL conc. HCl and stirred thoroughly. The brick red precipitate obtained was dissolved in methanol and loaded onto silica column and subsequently separated by flash chromatography (gradient elution up to 50% EtOAc in hexanes) to afford N-(4-(4-chlorobutanoyl)phenyl)acetamide (1c). Yellowish solid. Yield: 45%. 1H NMR (300 MHz, DMSO-d6) d 10.26 (s, 1H), 7.92 (2H, dd, J=6.5, 2.0 Hz), 7.71 (2H, dd, J=6.5, 2.4 Hz), 3.73-3.60 (2H, m), 3.10 (2H, t, J=6.8 Hz), 2.12-1.96 (5H, m). 13C NMR (75 MHz, DMSO-d6) d 197.85, 169.36, 144.13, 131.49, 129.58, 118.62, 45.34, 35.22, 27.39, 24.61.

N-(4-(4-chlorobutyl)phenyl)acetamide (1d)

A modified phenyl-keto reduction reaction described by West and colleagues [30] was followed to access alkylating agent 1d. In brief, to a stirred trifluoroacetic acid (1.5 mL) solution of N-(4-(4-chlorobutanoyl)phenyl)acetamide 1c (0.33 g, 1.3 mmol) was added triethylsilane (0.5 mL) gradually over 10 min keeping the temperature at room temperature. After addition, the mixture was allowed to stir for 15 min. The reaction was then quenched by neutralizing the trifluoroacetic acid with saturated $NaHCO_3$ solution. The mixture was extracted with $CH_2Cl_2$ (3×25 mL) and the organic layer pulled together, washed with brine, dried over $Na_2SO_4$, and concentrated in-vacuo to afford N-(4-(4-chlorobutyl)phenyl)acetamide 1d as a pale yellow solid. Yield: 77%. 1H NMR (300 MHz, DMSO-d6) d 9.83 (1H, s), 7.45 (2H, dd, J=8.8, 2.4 Hz), 7.08 (2H, dd, J=8.8, 2.4 Hz), 3.62 (2H, t, J=6.1 Hz), 2.52 (2H, t, J=7.0 Hz), 2.00 (3H, s), 1.78e1.50 (4H, m). 13C NMR (75 MHz, DMSO-d6) 168.48, 137.61, 136.75, 128.85, 119.48, 45.66, 34.07, 32.01, 28.63, 24.38.

General Alkylation Procedure

A mixture of alkylating agent (1.1 equiv), base (1.0 equiv) $K_2CO_3$ (1.1 equiv), and KI (catalytic) in DME (10 mL) was placed in a 20 mL microwave vial with a stirrer and tightly sealed. The mixture was subjected to microwave heating (Biotage, 120-140° C., 200-400 W, 15±5 bar) for 30-60 min. The mixture was directly purified on silica by flash chromatography (Hexanes: EtOAc gradient up to 70% EtOAc) to afford the titled compound. The free base where necessary, was converted to the HCl or oxalate salt.

Following the general alkylation reaction described above, alkylating agents 1c and 1d were reacted separately with 1-(pyridin-2-yl)piperazine to afford compounds 3 and 4, respectively.

N-(4-(4-(4-(pyridin-2-yl)piperazin-1-yl)butanoyl) phenyl) acetamide oxalate (3)

White amorphous powder. Yield: 48%. Mp: 140-142° C. 1H NMR (300 MHz, DMSO-d6) d 10.32 (1H, s), 8.18-8.10 (1H, m), 7.91 (2H, d, J=8.4 Hz), 7.71 (2H, d, J=8.5 Hz), 7.63-7.54 (1H, m), 6.92 (1H, d, J=8.6 Hz), 6.72 (1H, dd, J=7.1, 4.9 Hz), 3.86-3.62 (4H, m), 3.34-3.19 (4H, m), 3.17-3.07 (4H, m), 2.11-1.95 (5H, m). 13C NMR (75 MHz, DMSO-d6) d 197.59, 169.42, 163.37, 158.44, 148.02, 144.20, 138.36, 131.39, 129.62 (2C), 118.62, 114.55, 108.12, 55.69, 51.02 (2C), 42.42 (2C), 35.04, 24.62, 18.53. Anal. $C_{21}H_{26}N_4O_2 \cdot 2.4(COOH)_2$ (C, H, N).

N-(4-(4-(4-(pyridin-2-yl)piperazin-1-yl)butyl)phenyl)acetamide (4)

White crystals. Yield: 50%. Mp: 135-136° C. 1H NMR (300 MHz, DMSO-d6) d 9.82 (1H, s), 8.13-8.03 (1H, m), 7.50-7.41 (2H, m), 7.08 (2H, d, J=8.3 Hz), 6.76 (1H, d, J=8.6 Hz), 6.64-6.54 (2H, m), 3.47-3.38 (4H, m), 2.51 (2H, t, J=7.3 Hz), 2.42-2.33 (4H, m), 2.28 (2H, t, J=7.2 Hz), 2.00 (3H, s), 1.61e1.36 (4H, m). 13C NMR (75 MHz, DMSO-d6) d 168.44, 159.51, 147.96, 137.86, 137.49, 137.20, 128.82 (2C), 119.44 (2C), 113.34, 107.42, 58.17, 53.05 (2C), 45.09 (2C), 34.85, 29.33, 26.25, 24.38. Anal. $C_{21}H_{28}N_4O \cdot 0.20$ (C, H, N).

Deacetylation of compounds 3 and 4

Under acidic conditions following a slightly modified method described by Kilbourn and co-workers [31] afforded 1-(4-aminophenyl)-4-(4-(pyridin-2-yl)piperazin-1-yl)butan-1-one, 5 and 4-(4-(4-(pyridin-2-yl)piperazin-1-yl)butyl)aniline 6, respectively. Briefly, to an acetic acid (glacial, 7 mL) solution of the acetamide 3 or 4 (1 mmol) in a 20-mL microwave vial was added conc. HCl (3 mL). The homogeneous solution obtained was sealed and subjected to microwave heating (Biotage, 1450 C, 200-400 W, 10 bar) for 15-30 min. The internal pressure in the vial was released prior to opening and the content neutralized with saturated $NaHCO_3$ until slightly alkaline (pH=8). The aqueous mixture was extracted with CH2Cl2 (3×50 mL), organic layers pulled together, washed with brine (50 mL), dried over $Na_2SO_4$, and the excess solvent removed in-vacuo to afford the corresponding compounds 5 and 6 as free bases.

1-(4-aminophenyl)-4-(4-(pyridin-2-yl)piperazin-1-yl)butan-1-one (5)

White crystals. Yield: 78%. Mp: 203-204° C. 1H NMR (300 MHz, DMSO-d6) d 8.07 (1H, s), 7.67 (2H, dd, J=5.1, 1.8 Hz), 7.52e7.45 (1H, m), 6.77 (1H, d, J=8.8 Hz), 6.62-6.56 (1H, m), 6.54 (2H, dd, J=5.0, 1.8 Hz), 5.98 (2H, s), 3.43-3.37 (4H, m), 2.81 (2H, t, J=7.1 Hz), 2.40 (4H, t, J=5.1 Hz), 2.31 (2H, t, J=7.2 Hz), 1.81-1.70 (2H, m). 13C NMR (75 MHz, DMSO-d6) d 200.34, 161.63, 155.90, 150.05, 140.29, 132.98 (2C), 127.27, 115.70, 115.14 (2C), 109.81, 59.92, 54.98 (2C), 47.11 (2C), 37.38, 24.18. Anal. $C_{19}H_{24}N_4O$ (C, H, N).

4-(4-(4-(pyridin-2-yl)piperazin-1-yl)butyl)aniline (6)

White solid. Yield: 69%. Mp: 90-91° C. 1H NMR (300 MHz, DMSO-d6) d 8.07 (1H, d, J=4.9 Hz), 7.48 (1H, d, J=13.6 Hz), 6.87e6.72 (3H, m), 6.60 (1H, dd, J=7.0, 4.9 Hz), 6.51-6.42 (2H, m), 4.79 (2H, s), 3.41 (4H, t, J=5.1 Hz), 2.44-2.34 (6H, m), 2.27 (2H, t, J=7.0 Hz), 1.55-1.34 (4H, m). 13C NMR (75 MHz, DMSO-d6) d 159.51, 147.96, 146.76, 137.87, 129.57 (2C), 129.04, 114.39 (2C), 113.34, 107.43, 58.26, 53.05 (2C), 45.08 (2C), 34.70, 29.71, 26.25. Anal. $C_{19}H_{26}N_4 \cdot 3H_2O$ (C, H, N).

6-(4-chlorobutanoyl)-3,4-dihydroquinolin-2(1H)-one (2b)

Commercially available 3,4-dihydroquinolin-2(1H)-one 2a was acylated similarly as 1a to produce the intermediate 6-(4-chlorobutanoyl)-3,4-dihydroquinolin-2(1H)-one 2b as yellow crystals. Yield: 68%. 1H NMR (300 MHz, DMSO-d6) d 10.40 (1H, s), 7.78 (1H, s), 7.75 (1H, d, J=2.0 Hz), 6.91 (1H, d, J=8.2 Hz), 3.67 (2H, t, J=6.7 Hz), 3.07 (2H, t, J=7.1 Hz), 2.92 (2H, t, J=7.6 Hz), 2.47 (2H, t, J=6.5, 8.6 Hz), 2.04 (2H, q, J=6.9 Hz). 13C NMR (75 MHz, DMSO-d6) d 197.81, 170.88, 143.17, 130.86, 128.32, 128.16, 123.90, 115.22, 45.37, 35.20, 30.53, 27.43, 24.95.

6-(4-chlorobutyl)-3,4-dihydroquinolin-2(1H)-one (2c)

Deoxygenation of intermediate 2b following the TES-mediated reaction described above for 1d afforded the alkylating agent 2c in 50% yield. 1H NMR (300 MHz, DMSO-d6) d 9.99 (1H, s), 6.96-6.86 (2H, m), 6.77 (1H, d, J=7.2 Hz), 3.57 (2H, t, J=6.2 Hz), 2.78 (2H, t, J=7.0 Hz), 2.50-2.36 (4H, m), 1.72-1.57 (4H, m). 13C NMR (75 MHz, DMSO-d6) d 170.52, 136.60, 135.71, 127.94, 127.18, 123.80, 115.38, 45.53, 34.12, 32.05, 30.93, 28.74, 25.33.

The synthesis of compounds 7 and 8 followed the same alkylation general conditions as described above.

6-(4-(4-(pyridin-2-yl)piperazin-1-yl)butanoyl)-3,4-dihydroquinolin-2(1H)-one (7)

White crystalline solid. Yield: 71%. Mp: 192-193° C. 1H NMR (300 MHz, DMSO-d6) d 10.39 (1H, s), 8.07 (1H, d, J=4.4 Hz), 7.79 (2H, s), 7.48 (1H, ddd, J=2.1, 7.1, 8.9 Hz), 6.91 (1H, d, J=8.1 Hz), 6.76 (1H, d, J=8.6 Hz), 6.59 (1H, dd, J=4.8, 7.1 Hz), 3.43-3.33 (4H, m), 2.98-2.86 (4H, m), 2.47 (2H, t, J=7.7 Hz), 2.43-2.36 (4H, m), 2.32 (2H, t, J=7.1 Hz), 1.79 (2H, p, J=7.1 Hz). 13C NMR (75 MHz, DMSO-d6) d 198.81, 170.87, 159.50, 147.96, 142.92, 137.86, 131.33, 128.34, 128.18, 123.82, 115.18, 113.33, 107.42, 57.65, 52.93 (2C), 45.04 (2C), 35.76, 30.56, 24.99, 21.89. Anal. $C_{22}H_{26}N_4O_2$ (C, H, N).

6-(4-(4-(pyridin-2-yl)piperazin-1-yl)butyl)-3,4-dihydroquinolin-2(1H)-one (8)

Solid white crystals. Yield: 62%. Mp: 144-145° C. 1H NMR (300 MHz, DMSO-d6) d 9.98 (1H, s), 8.07 (1H, d, J=4.8 Hz), 7.49 (1H, dd, J=1.8, 6.8 Hz), 7.00-6.88 (2H, m), 6.81-6.70 (2H, m), 6.65-6.54 (1H, m), 3.45-3.38 (4H, m), 3.37-3.32 (3H, m), 2.84-2.75 (2H, m), 2.48 (2H, t, J=7.2 Hz), 2.44-2.33 (3H, m), 2.28 (2H, t, J=7.0 Hz), 1.59-1.47 (2H, m), 1.47-1.32 (2H, m). 13C NMR (75 MHz, DMSO-d6) d 170.51, 159.51, 147.96, 137.87, 136.50, 136.18, 128.01, 127.22, 123.79, 115.30, 113.34, 107.43, 58.19, 53.06 (2C), 45.10, 34.85, 30.95, 29.44, 26.31, 25.31, 25.22. Anal. $C_{22}H_{28}N_4O \cdot 8H_2O$ (C, H, N).

6-(3-chloropropoxy)-3,4-dihydroquinolin-2(1H)-one (3b)

A modified O-alkylation method reported by Rampa and colleagues [41] was followed to access intermediate 3b. Succinctly, 6-hydroxy-3,4-dihydroquinolin-2(1H)-one 3a (0.82 g, 5 mmol), 1-bromo-3-chloropropane (1 mL, 10 mmol), $K_2CO_3$, and KI (catalytic) were suspended in DME (15 mL) placed in a 20-mL Biotage microwave vial equipped with a vial. The vial was sealed and subjected to microwave heating (Biotage, 1300 C, 200 W, 5 bar) for 1 h. After this period, the vial was removed from the microwave, allowed to cool, internal pressure released and opened. The excess alkylating agent was removed in-vacuo and the residue purified directly on silica using a Combiflash® (gradient elution: up to 40% EtOAc in hexanes) to afford 6-(3-chloropropoxy)-3,4-dihydroquinolin-2(1H)-one, 3b (0.98 g, 82%) as white crystals. 1H NMR (300 MHz, DMSO-d6) d 9.88 (1H, s), 6.82-6.71 (3H, m), 4.00 (2H t, J=6.2 Hz), 3.75 (2H, t, J=6.8 Hz), 2.81 (2H, t, J=7.7 Hz), 2.38 (2H, t, J=7.7 Hz), 2.16-2.06 (2H, m). 13C NMR (75 MHz, DMSO-d6) d 170.18, 153.94, 132.37, 125.32, 116.21, 114.53, 113.47, 64.92, 42.46, 32.20, 30.78, 25.52.

Synthesis of Compounds 9 and 10 Used the Same Alkylation Conditions Described the General Alkylation Section Above.

6-(3-(4-(pyridin-2-yl)piperazin-1-yl)propoxy)-3,4-dihydroquinolin-2(1H)-one (9)

Using alkylating agent 3b and 1-(pyridin-2-yl)piperazine, compound 9 was obtained as its free base as white solid. Yield: 54%. Mp: 154-155° C. 1H NMR (300 MHz, DMSO-d6) d 9.88 (1H, s), 8.08 (1H, d, J=5.0 Hz), 7.49 (1H, ddd, J=8.9, 7.1, 2.0 Hz), 6.80-6.66 (4H, m), 6.60 (1H, dd, J=7.0, 4.9 Hz), 3.93 (2H, t, J=6.3 Hz), 3.44 (4H, t, J=5.0 Hz), 2.80 (2H, t, J=7.3 Hz), 2.47-2.41 (6H, m), 2.40-2.39 (1H, m), 2.38-2.35 (1H, m), 1.93-1.77 (2H, m). 13C NMR (75 MHz, DMSO-d6) d 170.17, 159.51, 154.25, 147.97, 137.87, 132.12, 125.26, 116.20, 114.46, 113.43, 113.36, 107.45, 66.51, 54.99, 53.07, 45.11, 30.81, 26.73, 25.55. Anal. $C_{21}H_{26}N_4O_2$ (C, H, N).

6-(3-(4-(pyridin-2-yl)-1,4-diazepan-1-yl)propoxy)-3,4-dihydroquinolin-2(1H)-one oxalate (10)

Using alkylating agent 3b and 1-(pyridin-2-yl)-1,4-diazepane as the amine, compound 10 was obtained as an oxalate salt. Yield: 30%. Mp: 190-192° C. 1H NMR (300 MHz, DMSO-d6) d 9.90 (1H, s), 8.08 (1H, d, J=4.8 Hz), 7.62-7.46 (1H, m), 6.86-6.51 (5H, m), 4.11-3.78 (4H, m), 3.64-3.47 (2H, m), 3.41-3.06 (6H, m), 2.80 (2H, t, J=7.4 Hz), 2.37 (2H, t, J=7.4 Hz), 2.26-1.96 (4H, m). 13C NMR (75 MHz, DMSO-d6) d 170.17, 163.94, 157.89, 153.79, 147.94, 138.13, 132.44, 125.30, 116.20, 114.55, 113.52, 112.66, 106.29, 65.67, 54.96, 54.05, 53.93, 45.61, 30.78, 25.52, 24.49, 24.19. Anal. $C_{22}H_{28}N_4O_2 \cdot 1.7(COOH)_2$ (C, H, N).

5-(3-chloropropoxy)-2,3-dihydro-1H-inden-1-one (4b)

Using similar O-alkylation reaction method described for 3b above, intermediate 4b was obtained as white solid crystal by reacting commercially available 5-hydroxy-2,3-dihydro-1H-inden-1-one, 4a with 1-bromo-3-chloropropane. Yield: 73%. 1H NMR (300 MHz, $CDCl_3$) d 7.64 (1H, d, J=8.3 Hz), 6.92-6.82 (2H, m), 4.16 (2H, t, J=5.8 Hz), 3.72 (2H, t, J=6.3 Hz), 3.04 (2H, t, J=5.7 Hz), 2.67-2.58 (2H, m), 2.31-2.17 (2H, m). 13C NMR (75 MHz, $CDCl_3$) d 205.17, 164.29, 158.13, 130.51, 125.29, 115.58, 110.29, 64.62, 41.25, 36.39, 31.97, 25.84.

5-(3-(4-(pyridin-2-yl)piperazin-1-yl)propoxy)-2,3-dihydro-1H-inden-1-one (11)

Following the general alkylation reaction described previously, intermediate 4b was reacted with 1-(pyridin-2-yl)piperazine to produce compound 11 as a white solid crystal. Yield: 68% Mp: 103-104° C. 1H NMR (300 MHz, DMSO-d6) d 8.08 (1H, s), 7.59-7.42 (2H, m), 7.04 (1H, s), 6.92 (1H, d, J=8.0 Hz), 6.76 (1H, d, J=8.6 Hz), 6.66-6.55 (1H, m), 4.10 (2H, t, J=6.3 Hz), 3.52-3.38 (4H, m), 3.05-2.95 (2H, m), 2.59-2.50 (4H, m), 2.00-1.80 (2H, m), 1.63-1.22 (4H, m). 13C NMR (75 MHz, DMSO-d6) d 204.58, 164.60, 159.49, 158.66, 147.98, 137.85, 130.21, 124.97, 116.02, 113.36, 110.99, 107.42, 66.86, 54.79, 53.05 (2C), 45.10 (2C), 36.44, 26.48, 25.90. Anal. $C_{21}H_{25}N_3O_2 \cdot 0.1H_2O$ (C, H, N).

1-(2,3-Dihydro-1H-inden-5-yl)-4-(4-(pyridin-2-yl)piperazin-1-yl)butan-1-one (12)

The commercially available indane, 5a was acylated under Friedel-Crafts acylation conditions and the intermediate 5b obtained was subsequently reacted with 1-(pyridin- 2-yl)piperazine under general N-alkylation conditions to afford the final compound 12 as white solid crystals. Yield: 59%, Mp: 74-75° C. 1H NMR (300 MHz, DMSO-d6) d 8.07 (1H, s), 7.78 (1H, s), 7.72 (1H, d, J=8.0 Hz), 7.52-7.42 (1H, m), 7.29 (1H, d, J=7.8 Hz), 6.73 (1H, d, J=8.6 Hz), 6.63-6.52 (1H, m), 3.44-3.30 (4H, m), 2.96 (2H, t, J=7.0 Hz), 2.91-2.79 (4H, m), 2.44-2.26 (6H, m), 2.06e1.92 (2H, m), 1.87-1.69 (2H, m). 13C NMR (75 MHz, DMSO-d6) d 199.95, 159.49, 149.82, 147.95, 144.70, 137.80, 135.89, 126.78, 124.69, 124.14, 113.29, 107.37, 57.63, 52.93 (2C), 45.03 (2C), 36.15, 32.85, 32.47, 25.42, 21.83. Anal. $C_{22}H_{27}N_3O$ (C, H, N).

5-Fluoro-2-(2-(4-(pyridin-2-yl)piperazin-1-yl)ethyl)-2,3-dihydro-1H-inden-1-one (13)

A mixture of 2-(2-chloroethyl)-5-fluoro-2,3-dihydro-1H-inden-1-one, 6a (1.1 g, 5.2 mmol), 1-(pyridin-2-yl)piperazine (0.90 g, 5.5 mmol), KI (100 mg), $NaHCO_3$(1.0 g, 11.9 mmol) in toluene (10 mL) was heated to reflux under $N_2$ for 12 h. After cooling to rt, the mixture was diluted with EtOAc (500 mL) and followed by washing with water (2×300 mL). The organic layer was dried over $Na_2SO_4$ and filtered. The filtrate was concentrated in vacuo to dryness and followed by column chromatography on silica gel afforded 5-fluoro-2-(2-(4-(pyridin-2-yl)piperazin-1-yl)ethyl)-2,3-dihydro-1H-inden-1-one, 13. The crystals were obtained by crystallization from EtOAc/Hexane in a yield of 26%. 1H NMR (300 MHz $CDCl_3$): 8.16 (1H, m), 7.73 (1H, dd, J=5.1, 8.1 Hz), 7.46 (1H, ddd, J=1.8, 6.9, 8.7 Hz), 7.02-7.13 (2H, m), 6.58-6.63 (2H, m), 3.38-2.90 (4H, m), 3.32 (1H, dd, J=7.5, 16.8 Hz), 2.86 (1H, dd, J=4.2, 16.8 Hz), 2.75-2.81 (1H, m), 2.45-2.60 (6H, m), 2.12-2.21 (1H, m), 1.78-1.88 (1H, m). 13C NMR (300 MHz, $CDCl_3$): 206.4, 167.0 (d, J=254.2 Hz), 159.5, 156.2 (d, J=10.4 Hz), 147.9, 137.4, 133.4, 126.0 (d, J=10.4 Hz), 115.6 (d, J=24.0 Hz), 113.2 (d, J=3.4 Hz), 112.9, 107.0, 55.7, 53.0 (2C), 45.6, 45.0 (2C), 32.2, 28.3. Anal. $C_{20}H_{22}FN_3O$ (C, H, N).

2-(2-Chloro-ethyl)-5-fluoro-indan-1-ol (7a)

To a solution of 2-(2-chloro-ethyl)-5-fluoro-indan-1-one (2 g, 9.4 mmol) and $CeCl_3$ (160 mg, 0.65 mmol) in MeOH (10 mL) was added with stirring NaBH4 (0.7 g, 18.5 mmol) at rt. After stirring at rt for 1 h, the mixture was diluted with EtOAc (200 mL) and washed with sat $NaHCO_3$(50 mL). The organic layer was dried over $Na_2SO_4$ and filtered. The filtrate was concentrated in vacuo and followed by column chromatography on silica gel afforded 2-(2-Chloro-ethyl)-5-fluoro-indan-1-ol, 1.85 g, yield=92%. 1H NMR (CDCl3): 7.33 (1H, m), 6.91 (2H, m), 4.82 (1H, brs), 3.73 (2H, m), 3.15 (1H, dd, J=7.2, 15.3 Hz), 2.50 (1H, m), 2.42 (1H, m), 2.34 (1H, m), 2.02 (1H, m).

5-Fluoro-2-[2-(4-pyridin-2-yl-piperazin-1-yl)-ethyl]-indan-1-ol (14)

A mixture of 2-(2-Chloro-ethyl)-5-fluoro-indan-1-ol (0.60 g, 2.8 mmol) 7a, 1-pyridin-2-yl-piperazine dihydrochloride (0.67 g, 2.84 mmol), KI (0.48 g), $K_2CO_3$ (1.2 g, 8.7 mmol) in DME (10 mL) was heated to reflux under $N_2$ for 12 h. Then the mixture was directly purified through column chromatography on silica gel afforded 5-fluoro-2-[2-(4-pyridin-2-yl-piperazin-1-yl)-ethyl]-indan-1-ol (14) which was converted to the hydroiodide salt. Crystallization from MeOH-Et₂O gave a solid, 0.6 g, yield 46%. Mp: 174-175° C. 1H NMR (DMSO-d6): 9.39 (1H, brs), 8.15 (1H, dd, J=1.5, 4.5 Hz), 7.60 (1H, dt, J=2.1, 8.7 Hz), 7.29 (1H, dd, J=5.4, 7.5 Hz), 6.97 (3H, m), 6.74 (1H, dd, J=4.8, 6.6 Hz), 5.52 (1H, brs), 4.68 (1H, brs), 4.38 (2H, brs), 3.59 (2H, brs), 3.04 (6H, m), 2.44 (1H, m), 2.08 (3H, m), 1.89 (1H, m). 13C NMR (150 MHz, CDCl3): 13C NMR (151 MHz, DMSO) d 162.47 (d, J=241.6 Hz, CeF), 158.33, 148.02, 143.64, 142.35, 138.45, 125.74, 114.75, 113.81, 111.74, 108.25, 79.02, 55.06, 48.01 (2C), 42.49 (2C), 40.57, 35.39, 27.38. Anal. $C_{20}H_{25}FIN_3O$ (C, H, N).

5-chloro-2-(2-(4-(pyridin-2-yl)piperazin-1-yl)ethyl)-2,3-dihydro-1H-inden-1-one (15)

Compound 15 was prepared similarly to 14 by reacting previously reported alkylating agent 5-chloro-2-(2-chloroethyl)-2,3-dihydro-1H-inden-1-one, 8a with 1-pyridin-2-yl-piperazine under same alkylation reaction conditions. The title compound was obtained as solid white crystal. Mp: 132-135° C. 1H NMR (300 MHz, DMSO-d6): 8.05 (1H, dd, J=1.8, 4.8 Hz), 7.66 (1H, s), 7.59 (1H, d, J=8.4 Hz), 7.48 (1H, dt, J=1.8, 8.4 Hz), 7.42 (1H, dd, J=1.8, 8.4 Hz), 6.75 (1H, d, J=8.1 Hz), 6.59 (1H, dd, J=5.4, 7.2 Hz), 3.18-3.28 (4H, m), 2.88 (1H, dd, J=4.2, 18.0 Hz), 2.70-2.79 (1H, m), 2.34-2.45 (4H, m), 2.25-2.33 (3H, m), 1.88-1.97 (1H, m), 1.74-1.86 (1H, m). 13C NMR (150 MHz, $CDCl_3$): 206.7, 159.4, 154.8, 147.9, 142.9, 137.4, 135.5, 128.1, 126.6, 124.9, 113.2, 107.0, 55.5, 52.9 (2C), 45.4, 45.0 (2C), 32.0, 28.2. Anal. $C_{20}H_{22}ClN_3O$ (C, H, N).

5-chloro-2-(2-chloroethyl)-2,3-dihydro-1H-indene (8b)

Amalgamated zinc was prepared by stirring a mixture of zinc (1.2 g), HgCl2 (120 mg) in 5 mL water with conc HCl (0.1 mL) at room temperature. After stirring for 5 min, the mixture was decanted and followed by adding in order water (1 mL), conc HCl (1.75 mL), toluene (10 mL), and starting material 5-chloro-2-(2-chloroethyl)-2,3-dihydro-1H-inden-1-one, 8a (2 g, 8.73 mmol). The mixture was refluxed with stirring for 12 h. The solid was filtered off, aqueous layer was diluted with EtOAc (200 mL), washed with water, and sat. $NaHCO_3$(50 mL). The organic layer was dried over $Na_2SO_4$ and filtered. The filtrate was concentrated in vacuo and used in the next step without further purification.

1-(2-(5-chloro-2,3-dihydro-1H-inden-2-yl)ethyl)-4-(pyridin-2-yl)piperazine (16)

A mixture of 5-chloro-2-(2-chloroethyl)-2,3-dihydro-1Hindene, 8b (1 g, 4.6 mmol), 1-(pyridin-2-yl)piperazine (0.9 g, 5.6 mmol), KI (100 mg), K2CO3 (1.2 g, 9.2 mmol) in DME (10 mL) was heated to reflux under $N_2$ for 12 h. Then the mixture was directly purified through column chromatography on silica gel to afforded the titled compound 1-(2-(5-chloro-2,3-dihydro-1H-inden-2-yl)ethyl)-4-(pyridin-2-yl)piperazine, 16 as an HCl salt after crystallization from MeOHeEt2O. Mp: 267-270° C. 1H NMR (300 MHz, $CD_3OD$) d 8.16 (1H, ddd, J=9.1, 7.1, 1.8 Hz), 8.12-8.04 (1H, m), 7.48 (1H, t, J=10.4 Hz), 7.28-7.01 (4H, m), 3.79 (4H, s), 3.58 (1H, dd, J=17.5, 7.8 Hz), 3.46 (1H, d, J=6.0 Hz), 3.30 (4H, s), 3.17-3.01 (2H, m), 2.77-2.60 (2H, m), 2.52 (1H, td, J=15.0, 7.5 Hz), 2.14-1.96 (2H, m). 13C NMR (151 MHz, $CD_3OD$) δ 152.35, 145.01, 144.72, 141.15, 136.92, 131.66, 126.11, 125.29, 124.14, 114.48, 113.12, 55.73, 50.42 (2C), 43.35 (2C), 38.26, 37.78, 37.63, 29.03. Anal. $C_{20}H_{24}ClN_3$·2HCl (C, H, N).

(E)-2-(6-chloro-1-oxo-1,3-dihydro-2H-inden-2-ylidene)acetic acid (9c)

A mixture of 6-chloro-2,3-dihydro-1H-inden-1-one (5 g, 30 mmol), glyoxylic acid (50% aqueous solution, 6.6 g, 72 mmol), and conc. $H_2SO_4$ (1 mL) in dioxane (5 mL) were stirred at refluxing temperature for 12 h. The mixture was cooled, the product filtered off, washed with water, and dried to give the acid (E)-2-(6-chloro-1-oxo-1,3-dihydro-2H-inden-2-ylidene)acetic acid, 9c as a white solid. 1H NMR (600 MHz, DMSO-d6): d 13.8 (1H, s), 7.86-7.58 (3H, m), 6.54 (1H, t, J=2.38 Hz) 4.05 (2H, s).

(E)-2-(5,6-dichloro-1-oxo-1,3-dihydro-2H-inden-2-ylidene)acetic acid (9d)

Preparation of intermediate 9d followed similar procedure as 9c to afford (E)-2-(5,6-dichloro-1-oxo-1,3-dihydro-2H-inden-2-ylidene)acetic acid (86%) as a white solid. 1H NMR (300 MHz, $CDCl_3$): d 7.97 (1H, s), 7.92 (1H, s), 6.50 (1H, s), 4.00 (2H, s).

2-(6-chloro-1-oxo-2,3-dihydro-1H-inden-2-yl)acetic acid (9e)

(E)-2-(6-Chloro-1-oxo-1,3-dihydro-2H-inden-2-ylidene) acetic acid, 9c (3 g, 13.4 mmol) in MeOH (30 mL) and dioxane (120 mL) with Pd/C (10%, 1 g) was stirred under $H_2$ (40 psi) for 48 h. The mixture was filtered through Celite and the solvent evaporated to give 2-(6-chloro-1-oxo-2,3-dihydro-1H-inden-2-yl)acetic acid as an off-white solid. 1H NMR (600 MHz, DMSO-d6): d 12.32 (1H, s), 7.7.75-7.51 (3H, m), 3.37-3.25 (1H, m), 2.94-2.83 (2H, m), 2.76-2.62 (2H, m).

2-(5,6-Dichloro-1-oxo-2,3-dihydro-1H-inden-2-yl)acetic acid (9f)

Synthesis of 9f followed same procedure as 9e to give 2-(5,6-dichloro-1-oxo-2,3-dihydro-1H-inden-2-yl)acetic acid as an off-white solid. 1H NMR (300 MHz, $CDCl_3$): d 12.32 (s, 1H), 7.91 (s, 1H), 7.82 (s, 1H), 3.36-3.28 (m, 1H), 2.97-2.79 (m, 2H), 2.72-2.68 (m, 2H).

2-(6-chloro-2,3-dihydrospiro[indene-1,2'-[1,3]dioxolan]-2-yl)ethan-1-ol (9 g)

A solution of 2-(6-chloro-1-oxo-2,3-dihydro-1H-inden-2-yl)acetic acid (1.1 g, 4.8 mmol), ethylene glycol (2 mL), TsOH (300 mg) in toluene (10 mL) was refluxed under $N_2$ for 48 h and $H_2O$ was removed by azeotropic distillation. The reaction was monitored by 1H NMR in a maximum conversion of 80% after which the reaction was quenched by addition of Et3N (1 mL), diluted with EtOAc (250 mL), washed with sat $NaHCO_3$, (25 mL) and $H_2O$ (25 mL). The organic layer was dried over anhydrous $Na_2SO_4$ and filtered. The filtrate was concentrated in vacuo to dryness and was used as such for the next reaction.

A solution of 2-(6-chloro-2,3-dihydrospiro [indene-1,2'-[1,3] dioxolan]-2-yl)acetic acid (1.3 g, 4.8 mmol) in dry THF (20 mL) was added dropwise to a suspension of LiAlH4 (0.37 g, 9.7 mmol) in dry THF (15 mL) at 0° C. and the resulting mixture was stirred at refluxing temperature for 12 h. EtOAc was added to quench excess $LiAlH_4$ and then aqueous HCl solution (10%, 50 mL) was added and the organic fraction separated. The aqueous solution was extracted with EtOAc (3×50 mL), and the combined organic fraction dried and the solvent evaporated to give alcohol 2-(6-chloro-2,3-dihydrospiro [indene-1,2'-[1,3]dioxolan]-2-yl)ethan-1-ol as a yellow oil which was used for the next step without further purification. 1H NMR (300 MHz, CDCl3): d 7.26e7.22 (2H, m), 7.14 (1H, s), 4.29-4.13 (4H, m), 3.77-3.73 (2H, m), 3.05-2.95 (1H, m), 2.69-2.63 (2H, m), 1.99-1.91 (1H, m), 1.77-1.63 (1H, m).

2-(5,6-Dichloro-2,3-dihydrospiro[indene-1,2'-[1,3]dioxolan]-2-yl)ethan-1-ol (9 h)

Preparation of 9 h followed the same procedure as 9 g to give the alcohol 2-(5,6-dichloro-2,3-dihydrospiro [indene-1,2'-[1,3]dioxolan]-2-yl)ethan-1-ol as a yellow oil which was used as such for the next step. 1H NMR (300 MHz, $CDCl_3$): d 7.36 (1H, s), 7.30 (1H, s), 4.26-4.22 (2H, m), 4.16-4.12 (4H, m), 3.05-2.95 (1H, m), 2.69-2.60 (2H, m), 1.99-1.91 (1H, m), 1.77-1.63 (1H, m).

2-(6-chloro-2,3-dihydrospiro[indene-1,2'-[1,3]dioxolan]-2-yl)ethyl 4-methylbenzenesulfonate (9i)

To a solution of 2-(6-chloro-2,3-dihydrospiro [indene-1,2'-[1,3] dioxolan]-2-yl)ethan-1-ol (0.55 g, 2.1 mmol), Et3N (0.66 mL, 6.3 mmol) in CH2Cl2 (10 mL) was added at room temperature p-TsCl (0.62 mg mL, 3.1 mmol). The mixture was stirred at room temperature for 12 h, and then followed by directly purification through column chromatography on silica gel and provided 2-(6-chloro-2,3-dihydrospiro [indene-1,2'-[1,3]dioxolan]-2-yl)ethyl 4-methylbenzenesulfonate, yield 95%. 1H NMR (300 MHz, $CDCl_3$):d 7.81 (2H, d, J=31.3 Hz), 7.37-7.32 (2H, d, J=31.3 Hz), 7.26-7.23 (2H, m), 7.10-7.08 (1H, m), 4.24-3.99 (6H, m), 2.93-2.83 (1H, m), 2.59-2.51 (2H, m), 2.46 (3H, s), 1.99-1.91 (1H, m), 1.77-1.63 (1H, m).

2-(5,6-Dichloro-2,3-dihydrospiro[indene-1,2'-[1,3]dioxolan]-2-yl)ethyl 4-methylbenzene sulfonate (9j)

Synthesis of alkylating agent 9j followed the same procedure as 9i. White solid. Yield 95%. 1H NMR (300 MHz, CDCl3): d 7.81 (1H, d, J=31.3 Hz), 7.37-7.32 (3H, m), 7.26 (1H, m), 4.23-3.97 (6H, m), 2.93-2.83 (1H, m), 2.59-2.51 (2H, m), 2.46 (3H, s), 1.99-1.91 (1H, m), 1.77-1.63 (1H, m).

6-chloro-2-(2-(4-(pyridin-2-yl)piperazin-1-yl)ethyl)-2,3-dihydro-1H-inden-1-one (17)

A mixture of 2-(6-chloro-2,3-dihydrospiro [indene-1,2'-[1,3] dioxolan]-2-yl)ethyl 4-methylbenzene sulfonate (263 mg, 0.64 mmol), 1-(pyridin-2-yl)piperazine (104 mg, 0.64 mmol), KI (50 mg), K2CO3 (266 mg, 1.9 mmol) in DME (10 mL) was heated 90° C. $N_2$ for 12 h. The reaction was diluted with EtOAc (25 mL), washed with sat $NaHCO_3$, (10 mL), water (10 mL). The organic layer was dried over $Na_2SO_4$ and filtered. The filtrate was concentrated in vacuo to dry and proceeded for the further reaction. The crude product was dissolved in wet MeOH, TsOH (25 mg) was added with stirring at rt. After stirring at rt for 12 h, the solution was diluted with EtOAc (50 mL) and followed by washing with sat $NaHCO_3$(10 mL). The organic layer was dried over $Na_2SO_4$ and filtered. The filtrate was concentrated in vacuo to dry and followed by column chromatography on silica gel afforded 6-chloro-2-(2-(4-(pyridin-2-yl)piperazin-1-yl)ethyl)-2,3-dihydro-1H-inden-1-one. The product was converted to a dihydrochloride salt, further crystallization from MeOH-Et2O afforded the target product. Mp: 161-164°

C., 1H NMR (600 MHz, CD3OD) d 8.23-8.06 (2H, m), 7.69 (2H, s), 7.59 (1H, d, J=7.9 Hz), 7.48 (1H, d, J=8.6 Hz), 7.15 (1H, s)), 3.64 (4H, d, J=31.1 Hz), 3.54-3.37 (3H, m), 3.32 (4H, s), 2.94 (2H, d, J=14.9 Hz), 2.39 (1H, s), 2.10 (1H, s). 13C NMR (151 MHz, CD$_3$OD) d 206.64, 152.90, 152.08, 144.49, 137.85, 137.40, 135.03, 133.66, 128.16, 122.91, 114.59, 112.73, 55.13, 50.67, 45.18 (2C), 43.32 (2C), 32.00, 25.03. Anal. C$_{20}$H$_{22}$ClN$_3$O·2HCl·1.2H$_2$O (C, H, N).

5,6-Dichloro-2-(2-(4-(pyridin-2-yl)piperazin-1-yl) ethyl)-2,3-dihydro-1H-inden-1-one (18)

Following similar procedure as compound 17, the target compound 5,6-dichloro-2-(2-(3,4-dihydroisoquinolin-2 (1H)-yl)ethyl)-2,3-dihydro-1H-inden-1-one, 18 was prepared in good yield, converted to hydrochloride salt and further crystallization from MeOH-Et2O to afford a white solid. Mp: 246-248° C. 1H NMR (600 MHz, DMSO-d6) d 11.63 (1H, s), 8.13 (1H, dd, J=5.6, 1.2 Hz), 7.97 (1H, s), 7.92 (1H, t, J=7.7 Hz), 7.86 (1H, s), 7.28 (1H, d, J=8.8 Hz), 6.95 (1H, t, J=6.3 Hz), 4.48 (3H, d, J=12.7 Hz), 3.45-3.29 (4H, m), 3.27-3.10 (4H, m), 3.01-2.89 (1H, m), 2.87 (1H, dd, J=17.4, 4.2 Hz), 2.35-2.24 (1H, m), 1.97 (1H, td, J=13.3, 4.4 Hz). 13 C NMR (151 MHz, DMSO-d6) d 205.22, 153.74, 142.32, 138.16, 136.49, 131.42, 129.60 (2C), 125.16 (2C), 114.43, 111.42, 53.97, 50.57, 45.26 (2C), 43.27 (2C), 32.09, 24.87. Anal. C$_{20}$H$_{21}$C$_{12}$N$_3$O·2HCl·H$_2$O (C, H, N).

5-chloro-1-(4-chlorophenyl)pentan-1-one (10a)

The procedure reported by Komissarov, V. V. et al. [35] was followed to afford 5-chloro-1-(4-chlorophenyl)pentan-1-one, 10a. Yield 71%. 1H NMR (300 MHz, CDCl3) d 7.90 (2H, d, J=9.0 Hz), 7.45 (2H, d, J=9.0 Hz), 3.59 (2H, t, J=6.0 Hz), 2.99 (2H, d, J=6.9 Hz), 1.85e1.91 (4H, m).

5-chloro-2-(3-chloropropyl)-2,3-dihydro-1H-inden-1-one (10b)

Using 5-chloro-1-(4-chlorophenyl)pentan-1-one 10a, the synthesis of 5-chloro-2-(3-chloropropyl)-2,3-dihydro-1H-inden-1-one 10b followed similar procedure as 6a. Yield 100%. 1H NMR (300 MHz, CDCl3) d 7.68 (1H, d, J ¼ 8.1 Hz), 7.46 (1H, s), 7.35 (1H, d, J=8.1 Hz), 3.56-3.61 (1H, m), 3.35 (1H, dd, J=7.8, 17.4 Hz), 2.77-2.84 (1H, m), 2.68-2.75 (1H, m), 2.00-2.08 (1H, m), 1.90-1.96 (2H, m), 1.66-1.75 (2H, m).

5-chloro-2-(3-(4-(pyridin-2-yl)piperazin-1-yl)propyl)-2,3-dihydro-1H-inden-1-one (19)

Following the general alkylation reaction described previously, compound 19 was prepared in moderate yield (yield 37%) as the hydrobromide salt. 1H NMR (DMSO-d6): 9.70 (2H, brs), 8.14 (1H, d, J=5.4 Hz), 7.80 (1H, dd, J=6.9, 8.1 Hz), 7.71 (1H, s), 7.64 (1H, d, J=8.1 Hz), 7.47 (1H, d, J=8.1 Hz), 7.15 (1H, d, J=8.7 Hz), 6.87 (1H, t, J=6.0 Hz), 4.37 (2H, d, J=14.7 Hz), 3.61 (2H, d, J=11.7 Hz), 3.25-3.40 (3H, m), 3.06-3.19 (4H, m), 2.72-2.88 (2H, m), 1.76-1.82 (3H, m), 1.48-1.55 (1H, m) 13C NMR (151 MHz, CD$_3$OD) d 207.52, 155.75, 153.11, 144.23, 141.34, 138.21, 134.77, 128.01, 126.70, 124.60, 114.61, 112.55, 56.54, 50.57 (2C), 46.53, 43.16 (2C), 32.14, 27.63, 21.40. Anal. C$_{21}$H$_{24}$ClN$_3$O·2HBr (C, H, N).

Ethyl 5-chloro-1-oxo-2,3-dihydro-1H-indene-2-carboxylate (11b)

A modified method described by Paccani and co-workers [42] was followed to access the 5-substituted b-keto ester 11b. In brief, a solution of the 5-chloro indanone 11a, (100 mmol, 1 equiv) in diethyl carbonate (50 mL) was added dropwise to a stirred suspension of NaH (200 mmol, 60% in mineral oil previously washed with hexanes) in diethyl carbonate (DEC) (25 mL) at 0° C. with stirring (note green coloration). When evolution of gas has ceased, the mixture was allowed to stir at room temperature overnight. The mixture was then diluted in CH2Cl2 and treated with aqueous acetic acid solution. The aqueous phase was separated and extracted with CH$_2$Cl$_2$. The combined organic extracts were dried (Na$_2$SO$_4$) and concentrated under reduced pressure to yield the brown thick oil crude. The crude was loaded onto a cartridge and purified using flash chromatography with a gradient elution (up to 10% EtOAc in hexanes) to afford ethyl 5-chloro-1-oxo-2,3-dihydro-1H-indene-2-carboxylate, 11b. Needle-like white crystals. Yield: 89%. 1H NMR (300 MHz, CDCl$_3$) d 10.47-10.20 (1H, m), 7.65-7.40 (6H, m), 4.31-4.13 (4H, m), 3.71-3.64 (1H, m), 3.55-3.38 (2H, m), 3.37-3.22 (2H, m), 1.35-1.19 (6H, m). 13C NMR (75 MHz, CDCl$_3$) d 198.15, 168.59, 155.11, 144.83, 135.83, 134.08, 131.40, 130.78, 130.06, 129.88, 129.80, 127.98, 125.70, 123.71, 121.81, 102.72, 61.83, 60.23, 53.24, 32.40, 29.91, 14.42, 14.17.

Ethyl 5-chloro-2-(4-chlorobutyl)-1-oxo-2,3-dihydro-1Hindene-2-carboxylate (11c)

To a suspension of hexane washed NaH (60% in mineral oil, 12 mmol) in dry DMF was added a solution of ethyl 5-chloro-1-oxo-2,3-dihydro-1H-indene-2-carboxylate 11b (10 mmol) dropwise with stirring (note the green coloration) over 30 min. After the evolution of gas has ceased, the 1-bromo-4-chlorobutane (20 mmol) was added dropwise and allowed to stir for 18-24 h. After, the reaction was quenched in water (100 mL), shaken with CH$_2$Cl$_2$ (2×100 mL), the organic layers pulled together, washed with brine, and dried over Na$_2$SO$_4$ and concentrated in-vacuo to obtain the crude product which was then used directly in the next step without further purification.

5-chloro-2-(4-chlorobutyl)-2,3-dihydro-1H-inden-1-one (11d)

Generally, an acid catalyzed decarboxylation of the tertiary β-keto ester was followed under microware heating conditions to afford alkylation agent 11d in good to moderate yield. Briefly, the crude β-keto ester 11c was dissolved in 10 mL of glacial acetic acid and transferred into a 20 mL Biotage microwave vial equipped with a stirrer. To this homogenous solution was added 3 mL of conc. HCl. The vial was sealed and subjected to microwave heating (Biotage, 120° C., 200 W, 18 bar) for 30 min. The vial was then allowed to cool to room temperature and internal pressure released prior to opening. The content was neutralized with saturated NaHCO$_3$ and extracted with CH$_2$Cl$_2$ (3×50 mL). The organic layers were pulled together, washed with brine, dried (Na$_2$SO$_4$), and solvent removed in-vacuo to produce a thick, oily crude. The crude was purified on flash column chromatography using gradient elution (up to 20% EtOAc in hexanes) to afford the corresponding alkylating agent 11d as a clear yellowish oil. Yield (overall over 2 steps): 51%. 1H NMR (300 MHz, CDCl3) d 7.63 (1H, dd, J=8.1, 1.4 Hz), 7.41 (1H, dd, J=1.9, 1.0 Hz), 7.30 (1H, dd, J=8.2, 1.8), 3.52 (2H, tt, J=6.6, 1.0 Hz), 3.29 (1H, ddt, J=17.4, 7.9, 0.8 Hz), 2.84-2.59 (2H, m), 1.99-1.85 (1H, m), 1.85-1.72 (2H, m), 1.63-1.50 (2H, m), 1.50-1.39 (1H, m). 13C NMR (75 MHz, CDCl$_3$) d 205.96, 154.61, 141.28, 134.76, 128.28, 126.65, 124.98, 45.00, 43.03, 34.06, 32.54.

5-chloro-2-(4-(4-(pyridin-2-yl)piperazin-1-yl)butyl)-2,3-dihydro-1H-inden-1-one (20)

Using 11d as the alkylating agent, compound 20 was prepared under the same general alkylation procedure. The final compound 20 was converted to its HCl salt to obtain a white flaky solid. Yield: 72%, Mp: 233-234° C. 1H NMR (300 MHz, DMSO-d6) d 11.63 (2H, s), 8.08 (1H, d, J=1.5, 5.9 Hz), 7.99 (1H, d, J=8.0 Hz), 7.66 (1H, s), 7.62 (1H, d, J=8.1 Hz), 7.45 (1H, dd, J=1.6, 8.2 Hz), 7.36 (1H, d, J=9.0 Hz), 6.98 (1H, d, J=6.4 Hz), 3.73-3.49 (4H, m), 3.31 (1H, dd, J=7.7, 17.5 Hz), 3.10 (4H, q, J=8.9, 11.0 Hz), 2.91-2.65 (2H, m), 1.93-1.63 (4H, m), 1.61-1.21 (4H, m). 13C NMR (75 MHz, DMSO-d6) d 207.25, 159.52, 156.23, 147.96, 140.13, 137.85, 135.50, 128.32, 127.35, 125.13, 113.33, 107.43, 58.21, 53.04 (2C), 47.30, 45.11 (2C), 32.53, 30.99, 26.68, 25.10. Anal. C$_{22}$H$_{26}$ClN$_3$O·2HCl (C, H, N).

Ethyl 5-chloro-2-methyl-1-oxo-2,3-dihydro-1H-indene-2-carboxylate (12a)

To a stirred suspension of NaH (15 mmol, 60% in mineral oil previously washed with hexanes) in dry DMF was added a solution of ethyl 5-chloro-1-oxo-2,3-dihydro-1H-indene-2-carboxylate 11b (7.5 mmol) in dry DMF portion-wise under N$_2$. After stirring for 2 h, iodomethane (15 mmol) was added dropwise and the reaction stirred for 24 h. The reaction was quenched with water (50 mL), extracted with CH$_2$Cl$_2$ (2×50 mL), the organic layers pulled together was washed with brine, dried over Na$_2$SO$_4$ and the solvent removed under reduced pressure to obtain the crude product which was loaded onto a cartridge and purified by flash chromatography using a gradient of up to 5% EtOAc in hexanes to obtain compound the intermediate compound. Yield: 60%; 1H NMR (300 MHz, CDCl3) d 7.54 (1H, d, J=8.1 Hz), 7.34 (1H, s), 7.22 (1H, d, J=8.5 Hz), 3.99 (2H, q, J=7.4 Hz), 3.56 (1H, d, J=17.3 Hz), 2.85 (1H, d, J=17.3 Hz), 1.36 (3H, s), 1.13-0.99 (3H, m).

5-chloro-2-methyl-2,3-dihydro-1H-inden-1-one (12b)

Ethyl 5-chloro-2-methyl-1-oxo-2,3-dihydro-1H-indene-2-carboxylate, 12a (2.2 mmol) was subsequently hydrolyzed and decarboxylated by dissolving it in acetic acid (5 mL) and concentrated HCl (2 mL) was added and transferred into a 20 mL-microwave vial with a stirrer and tightly sealed. The mixture was heated in the microwave at 80° C. for 1 h, the reaction was allowed to cool to room temperature, basified with NaHCO$_3$ solution and extracted with CH$_2$Cl$_2$. The organic layer was washed with brine, dried over Na$_2$SO$_4$ and the solvent removed under reduced pressure. The crude was loaded onto a cartridge and purified by flash chromatography using a gradient of 5% EtOAc in hexanes to afford 12b. Yield: 79%; 1H NMR (300 MHz, CDCl$_3$) d 7.61 (1H, d, J=8.6 Hz), 7.38 (1H, s), 7.28 (1H, d, J=8.0 Hz), 3.40-3.25 (1H, m), 2.71-2.61 (2H, m), 1.26 (3H, d, J=7.3 Hz).

6-chloro-2-(3-chloropropyl)-2-methyl-2,3-dihydro-1Hinden-1-one, 12c and 6-chloro-2-(4-chlorobutyl)-2-methyl-2,3-dihydro-1H-inden-1-one (12d)

A solution of the 12b (3.32 mmol) in dry DMF was added dropwise to a stirred suspension of NaH (9.96 mmol, 60% in mineral oil previously washed with hexanes) in dry DMF. After the reaction mixture was stirred for an hour, dihaloaklylhalide (1-bromo-3-chloropropane for 12c or 1-bromo-4-chlorobutane for 12d) (6.64 mmol) was added dropwise and stirred overnight. The reactions were quenched in water, extracted with CH$_2$Cl$_2$, the organic layer washed with brine, dried over Na$_2$SO$_4$, and concentrated under reduced pressure to obtain the crude product which was used in the next step without further purification.

6-chloro-2-methyl-2-(3-(4-(pyridin-2-yl)piperazin-1-yl)propyl)-2,3-dihydro-1H-inden-1-one (21)

The crude alkylating agent 12c was reacted with pyridinylpiperazine under the general N-alkylation reaction conditions described above to afford compound 21 as a solid. Yield: 62%. Mp: 232-233.6° C. 1H NMR (300 MHz, CDCl$_3$) d 8.17 (1H, d, J=4.7 Hz), 7.67 (1H, d, J=8.2 Hz), 7.45 (2H, d, J=8.7 Hz), 7.35 (1H, d, J=7.9 Hz), 6.62 (2H, d, J=8.1 Hz), 3.51 (4H, s), 3.11 (1H, d, J=17.3 Hz), 2.87 (1H, d, J=17.6 Hz), 2.51 (4H, s), 2.33 (2H, d, J=7.3 Hz), 2.07-1.99 (1H, m), 1.61 (3H, t, J=7.6 Hz), 1.22 (3H, s). 13C NMR (151 MHz, CD$_3$OD) d 209.76, 154.72, 152.26, 145.04, 141.56, 136.75, 133.97, 128.15, 126.87, 125.00, 114.45, 113.15, 56.79, 50.37 (2C), 43.25, 43.23 (2C), 39.30, 34.19, 22.84, 19.15. Anal. C$_{22}$H$_{26}$ClN$_3$O·2HCl·H$_2$O (C, H, N).

6-chloro-2-methyl-2-(4-(4-(pyridin-2-yl)piperazin-1-yl)butyl)-2,3-dihydro-1H-inden-1-one (22)

The crude alkylating agent 12d was reacted with pyridinylpiperazine in a similar manner as described for 21 to afford under the general N-alkylation reaction conditions described previously to afford compound 22 as a solid. Yield: 52%. Mp: 214-215.9° C.; 1H NMR (300 MHz, CDCl3) d 8.20e8.13 (1H, m), 7.70-7.62 (1H, m), 7.50-7.42 (2H, m), 7.38-7.22 (1H, m), 6.70-6.54 (2H, m), 3.52 (5H, t, J=4.8 Hz), 3.09 (1H, d, J=17.5 Hz), 2.85 (1H, d, J=17.5 Hz), 2.50 (4H, t, J=5.2 Hz), 2.39-2.27 (2H, m), 2.09-1.92 (1H, m), 1.68-1.47 (4H, m), 1.20 (3H, d, J=1.8 Hz). 13C NMR (151 MHz, CD3OD) d 210.38, 154.89, 145.04, 141.43, 136.76, 134.23 (2C), 128.06, 126.77, 124.85, 114.43, 113.15, 56.48, 50.32 (2C), 49.00, 43.24, 43.21.

Receptor Binding Affinity Studies

Binding affinities reported in Tables 1-3 were conducted by the National Institute of Mental Health Psychoactive Drug Screening Program (NIMH-PDSP). Details of the methods and radioligands used for the binding assays were previously reported [43]. [$^{35}$S]GTPγS binding.

The method from Newman-Tancredi et al. [44], was adapted for assessment of the functional status of compound 21 as follows: To prepare the membranes, five 15 cm plates of HEK-h5HT$_{1A}$ cells, 80-90% confluent, provided enough membranes for one assay plate (4 drug curves). GTPgS assay buffer (20 mM HEPES, pH 7.4, 10 mM MgCl2, 100 mM NaCl, and 0.2 mM DTT) was used throughout the assay. The cells were scraped from the plates into buffer, centrifuged at 200 rpm for 15 min, the supernatant was removed, and the pellet was homogenized in 10 mL buffer/plate of cells. The homogenate was centrifuged at 17,500 rpm for 15 min, and the resulting pellet was washed 2 times by homogenization in 10 mL buffer and centrifugation to remove serotonin that was present in the growth medium. The supernatant was removed, and the final pellet from 5 plates was resuspended in 10 mL of assay buffer.

Cell membranes (40-75 µg protein) were preincubated (10 min, room temperature) with test compound in duplicate in assay buffer. The reaction was initiated by the addition of GDP (3 mM) and [$^{35}$S]GTPγS (0.1 nM, 1350 Ci/mmol, PerkinElmer, ~150,000 cpm) in a final volume of 1 mL. The reaction was incubated for 60 min at room temperature on a rotating platform. Non-specific binding is defined with 1 mM WAY-100635. Agonist efficacy is expressed relative to that of 5-HT tested at a maximally effective concentration (100 nM) in each experiment. A dose response curve with the prototypical full agonist serotonin was conducted in each experiment to identify full and partial agonist compounds. Experiments were terminated by rapid filtration over Filtermat A with ice-cold saline using a Tomtec harvester and radioactivity determined using a PerkinElmer microbetaplate counter. EC50 values are calculated with GraphPad Prism and maximal effect for a given drug each day is normalized to the maximal effect of serotonin.

HEK-5-HT$_{7A}$/cAMP Functional Assay

Human embryonic kidney cells were transfected with 10 mg h5-HT7A cDNA using PEI in unsupplemented DMEM. After 5 h, cells were plated at a density of 200,000 cells per well in 48 well plates in DMEM supplemented with 10% charcoal-stripped FetalClone and pen-strep. The medium was removed about 18 h later. For agonist assays, 0.9 mL EBSS (116 mM NaCl, 22 mM glucose, 15 mM HEPES, 8.7 mM NaH2PO4, 5.4 mM KCl, 1.3 mM CaCl$_2$), 1.2 mM MgSO4, 1 mM ascorbic acid, 0.5 mM IBMX [3-isobutyl-1-methyl-xanthine] without BCS, pH 7.4 at 37° C.) was added. After 20 min, the compound was added in a final volume of 1 mL, and incubated for 20 min. For antagonists, 0.8 mL EBSS is added, cells were incubated for 10 min, the compound was added, and incubated for 10 min after which serotonin (100 nM) was added. For all conditions, after 20 min incubation with agonist, the reaction was terminated by aspiration of the buffer, and 0.1 mL trichloroacetic acid was added.

Plates were incubated for 2 h on a rotator. Adenylate cyclase activity was measured using a cyclic AMP EIA kit (Cayman). Aliquots (40 ml) of each well were diluted to 200 ml with EIA buffer from the kit, and 50 ml of the dilution was added to the EIA plate. After addition of tracer and monoclonal antibody, the EIA plates were incubated for 18 h at 4° C. The reaction was aspirated, plates were washed 5×300 ml with wash buffer, and Ellman's reagent was added. After a 2-h incubation in the dark on a rotator, the plates were read at 410 nm. Basal cAMP is subtracted from all values. 5-HT$_{7A}$ agonists stimulate cAMP formation, maximal stimulation was defined with 10 mM serotonin. The maximal drug effect is normalized to maximal serotonin effect in the tables. For antagonists, maximal inhibition of cAMP formation is defined with 10 mM lurasidone.

Data Analysis

For functional assays, GraphPAD Prism was used to calculate either EC$_{50}$ (agonists) or IC$_{50}$ (antagonists) values using data expressed as pg cAMP for adenylate cyclase activity, % serotonin stimulation for GTPγS binding.

Example 1—Treatment of Depression (Prophetic)

A 40-year-old female patient presents with symptoms including a feeling of sadness, loss of interest, difficulty sleeping, difficulty concentrating, and thoughts of suicide. The patient is diagnosed with depression and administered a composition having a therapeutically effective amount of 5-chloro-2-methyl-2-(3-(4-(pyridin-2-yl) piperazin-1-yl) propyl)-2,3-dihydro-1H-inden-1-one (Compound 21) for a time period sufficient to alleviate the symptoms. The patient's symptoms are monitored closely over the period of several months with a noticeable decrease in symptoms.

Example 2—Treatment of Anxiety (Prophetic)

A 30-year-old female patient presents with symptoms of difficulty in concentrating, nervousness, restlessness, increased heart rate, and having feelings of panic. The patient is diagnosed with anxiety and administered a composition having a therapeutically effective amount of 5-chloro-2-methyl-2-(3-(4-(pyridin-2-yl) piperazin-1-yl) propyl)-2,3-dihydro-1H-inden-1-one (Compound 21) for a time period sufficient to alleviate the symptoms. The patient's symptoms are monitored closely over the period of several months with a noticeable decrease in symptoms.

Example 3—Treatment of Schizophrenia (Prophetic)

A 26-year-old male patient reports having delusions and hallucinations. The patient exhibits disorganized thinking, behavior, and speech. The patient is administered a composition having a therapeutically effective amount of 5-chloro-2-methyl-2-(3-(4-(pyridin-2-yl) piperazin-1-yl)propyl)-2,3-dihydro-1H-inden-1-one (Compound 21) for a time period sufficient to alleviate the symptoms. The patient's symptoms are monitored closely over the period of several months with a noticeable decrease in symptoms.

Example 4—Treatment of Cognitive Impairment Associated with Alzheimer's Disease (Prophetic)

A 68-year-old male patient presents with memory loss, confusion, difficulty completing familiar tasks, and difficulty understanding visual images and spatial relationships. The patient is diagnosed with Alzheimer's disease and administered a composition having a therapeutically effective amount of 5-chloro-2-methyl-2-(3-(4-(pyridin-2-yl) piperazin-1-yl)propyl)-2,3-dihydro-1H-inden-1-one (Compound 21) for a time period sufficient to reduce the severity of the symptoms.

CONCLUSION

The inventors have developed numerous N-alkyl substituted pyridinyl-piperazine compounds capable of being used to treat neurological disorders characterized by cognitive and anxiolytic impairments. The highest binding affinities were found with 5-chloro-2-methyl-2-(3-(4-(pyridin-2-yl) piperazin-1-yl)propyl)-2,3-dihydro-1H-inden-1-one (Compound 21).

REFERENCES

[1] A. Serretti, D. De Ronchi, C. Lorenzi, D. Berardi, New antipsychotics, and schizophrenia: a review on efficacy and side effects, Curr. Med. Chem. 11 (3) (2004) 343-358.

[2] M. C. Mauri, S. Paletta, M. Maffini, A. Colasanti, F. Dragogna, C. Di Pace, A. C. Altamura, Clinical pharmacology of atypical antipsychotics: an update, EXCLI J 13 (2014) 1163-1191.

[3] A. Attard, D. M. Taylor, Comparative effectiveness of atypical antipsychotics in schizophrenia: what have real-world trials taught us? CNS Drugs 26 (6) (2012) 491-508.

[4] J. M. Palacios, A. Probst, R. Cortes, The distribution of serotonin receptors in the human brain: high density of [3H]LSD binding sites in the raphe nuclei of the brainstem, Brain Res. 274 (1) (1983) 150-155.

[5] R. L. Carhart-Harris, D. J. Nutt, Serotonin and brain function: a tale of two receptors, J. Psychopharmacol. 31 (9) (2017) 1091-1120.

[6] N. M. Barnes, T. Sharp, A review of central 5-HT receptors and their function, Neuropharmacology 38 (8) (1999) 1083-1152.

[7] D. Baldwin, S. Rudge, The role of serotonin in depression and anxiety, Int. Clin. Psychopharmacol. 9 (Suppl 4) (1995) 41-45.

[8] J. J. Mann, Role of the serotonergic system in the pathogenesis of major depression and suicidal behavior, Neuropsychopharmacology 21 (1) (1999) 99-105.

[9] R. A. Bantick, J. F. Deakin, P. M. Grasby, The $5\text{-HT}_{1A}$ receptor in schizophrenia: a promising target for novel atypical neuroleptics? J. Psychopharmacol. 15 (1) (2001) 37-46.

[10] H. Rollema, Y. Lu, A. W. Schmidt, S. H. Zorn, Clozapine increases dopamine release in prefrontal cortex by $5\text{-HT}_{1A}$ receptor activation, Eur. J. Pharmacol. 338 (2) (1997) R3-R5.

[11] Y. Ohno, New insight into the therapeutic role of $5\text{-HT}_{1A}$ receptors in central nervous system disorders, Cent. Nerv. Syst. Agents Med. Chem. 10 (2) (2010) 148-157.

[12] S. Ramboz, R. Oosting, D. A. Amara, H. F. Kung, P. Blier, M. Mendelsohn, J. J. Mann, D. Brunner, R. Hen, Serotonin receptor 1A knockout: an animal model of anxiety-related disorder, Proc. Natl. Acad. Sci. U.S.A 95 (24) (1998) 14476-14481.

[13] L. K. Heisler, H. M. Chu, T. J. Brennan, J. A. Danao, P. Bajwa, L. H. Parsons, L. H. Tecott, Elevated anxiety and antidepressant-like responses in serotonin $5\text{-HT}_{1A}$ receptor mutant mice, Proc. Natl. Acad. Sci. U.S.A 95 (25) (1998) 15049-15054.

[14] S.-M. Wang, C. Han, S.-J. Lee, A. A. Patkar, P. S. Masand, C.-U. Pae, Vilazodone for the treatment of depression: an update, Chonnam Med. J. 52 (2) (2016) 91-100.

[15] J. E. Frampton, Vilazodone: in major depressive disorder, CNS Drugs 25 (7) (2011) 615-627.

[16] M. N. Modica, E. Lacivita, S. Intagliata, L. Salerno, G. Romeo, V. Pittala, M. Leopoldo, Structure-activity relationships and therapeutic potentials of 5-HT(7) receptor ligands: an update, J. Med. Chem. 61 (19) (2018) 8475-8503.

[17] J. D. Glass, G. H. Grossman, L. Farnbauch, L. DiNardo, Midbrain raphe modulation of nonphotic circadian clock resetting and 5-HT release in the mammalian suprachiasmatic nucleus, J. Neurosci. 23 (20) (2003) 7451-7460.

[18] P. B. Hedlund, J. G. Sutcliffe, Functional, molecular and pharmacological advances in 5-HT7 receptor research, Trends Pharmacol. Sci. 25 (9) (2004) 481-486.

[19] A. J. Roberts, P. B. Hedlund, The 5-HT(7) receptor in learning and memory, Hippocampus 22 (4) (2012) 762-771.

[20] A. I. Abbas, P. B. Hedlund, X. P. Huang, T. B. Tran, H. Y. Meltzer, B. L. Roth, Amisulpride is a potent 5-HT7 antagonist: relevance for antidepressant actions in vivo, Psychopharmacology 205 (1) (2009) 119-128.

[21] V. S. Naumenko, N. K. Popova, E. Lacivita, M. Leopoldo, E. G. Ponimaskin, Interplay between serotonin $5\text{-HT}_{1A}$ and 5-HT7 receptors in depressive disorders, CNS Neurosci. Ther. 20 (7) (2014) 582-590.

[22] D. Hoyer, J. P. Hannon, G. R. Martin, Molecular, pharmacological and functional diversity of 5-HT receptors, Pharmacol. Biochem. Behav. 71 (4) (2002) 533-554.

[23] U. Renner, A. Zeug, A. Woehler, M. Niebert, A. Dityatev, G. Dityateva, N. Gorinski, D. Guseva, D. Abdel-Galil, M. Fröhlich, F. Döring, E. Wischmeyer, D. W. Richter, E. Neher, E. G. Ponimaskin, Heterodimerization of serotonin receptors $5\text{-HT}_{1A}$ and 5-HT7 differentially regulates receptor signalling and trafficking, J. Cell Sci. 125 (Pt 10) (2012) 2486-2499.

[24] P. Bernstein, Successful drug discovery volume 3, in: Janos Fischer, Christian Klein, Wayne E. Childers (Eds.), ChemMedChem 13 (18) (2018).

[25] A. Rague, K. Tidgewell, Pharmacophore comparison and development of recently discovered long chain arylpiperazine and sulfonamide based 5-HT7 ligands, Mini Rev. Med. Chem. 18 (7) (2018) 552-560.

[26] K. Peprah, X. Y. Zhu, S. V. K. Eyunni, V. Setola, B. L. Roth, S. Y. Ablordeppey, Multireceptor drug design: haloperidol as a scaffold for the design and synthesis of atypical antipsychotic agents, Bioorg. Med. Chem. 20 (3) (2012) 1291-1297.

[27] D. Sampson, X. Y. Zhu, S. V. Eyunni, J. R. Etukala, E. Ofori, B. Bricker, N. S. Lamango, V. Setola, B. L. Roth, S. Y. Ablordeppey, Identification of a new selective dopamine D4 receptor ligand, Bioorg. Med. Chem. 22 (12) (2014) 3105-3114.

[28] B. A. Bricker, K. Peprah, H. J. Kang, S. Y. Ablordeppey, Evaluation of SYA16263 as a new potential antipsychotic agent without catalepsy, Pharmacol. Biochem. Behav. 179 (2019) 55-62.

[29] S. Y. Ablordeppey, X. Y. Zhu, Identification of Agents Displaying Functional Activation of Dopamine D2 and D4 Receptors and Methods for Treatment of Psychosis, Patent WO 2018148529A1, 2018.

[30] C. T. West, S. J. Donnelly, D. A. Kooistra, M. P. Doyle, Silane reductions in acidic media. II. Reductions of aryl aldehydes and ketones by trialkylsilanes in trifluoroacetic acid. Selective method for converting the carbonyl group to methylene, J. Org. Chem. 38 (15) (1973) 2675-2681.

[31] M. R. Kilbourn, M. J. Welch, C. S. Dence, T. J. Tewson, H. Saji, M. Maeda, Carrier added and no-carrier-added syntheses of [18F]spiroperidol and [18F]haloperidol, Int. J. Appl. Radiat. Isot. 35 (7) (1984) 591-598.

[32] E. Ofori, X. Y. Zhu, J. R. Etukala, B. A. Bricker, S. Y. Ablordeppey, Synthesis and evaluation of the structural elements in alkylated tetrahydroisoquinolines for binding to CNS receptors, Bioorg. Med. Chem. 24 (22) (2016) 5730-5740.

[33] K. Peprah, X. Y. Zhu, S. V. Eyunni, J. R. Etukala, V. Setola, B. L. Roth, S. Y. Ablordeppey, Structure-activity relationship studies of SYA 013, a homopiperazine analog of haloperidol, Bioorg. Med. Chem. 20 (5) (2012) 1671-1678.

[34] J. L. Luche, Lanthanides in organic chemistry. 1. Selective 1,2 reductions of conjugated ketones, J. Am. Chem. Soc. 100 (7) (1978) 2226-2227.

[35] V. V. Komissarov, E. S. Kniazhanskaia, A. V. Atrokhova, M. B. Gottikh, A. M. Kritsyn, [The search of novel inhibitors of HIV-1 integrase among 5-(4-halogenophenyl)-5-oxopentyl derivatives of nucleic bases], Bioorg. Khim. 40(5) (2014) 578-587.

[36] U. Jordis, J. Frohlich, M. Treu, M. Hirnschall, L. Czollner, B. Kalz, S. Welzig, Derivatives and Analogs of Galanthamine, Patent Number US2007027138A1, 2007.

[37] E. K. Onyameh, B. A. Bricker, E. Ofori, S. Y. Ablordeppey, Enantioseparation of 5-chloro-2-{2-[3,4- dihydroisoquinoline-2(1H)-yl]ethyl}-2-methyl-2,3-dihydro-1H-inden-1-one (SYA 40247), a high-affinity 5-HT (7) receptor ligand, by HPLC-PDA using amylose tris-(3, 5-dimethylphenylcarbamate) as a chiral stationary phase, Biomed. Chromatogr. 33 (9) (2019), e4565.

[38] E. Ofori, X. Y. Zhu, J. R. Etukala, K. Peprah, K. R. Jordan, A. A. Adkins, B. A. Bricker, H. J. Kang, X. P. Huang, B. L. Roth, S. Y. Ablordeppey, Design and synthesis of dual 5-$HT_{1A}$ and 5-HT7 receptor ligands, Bioorg. Med. Chem. 24 (16) (2016) 3464-3471.

[39] G. Zhang, C. Liu, H. Yi, Q. Meng, C. Bian, H. Chen, J. X. Jian, L. Z. Wu, A. Lei, External oxidant-free oxidative cross-coupling: a photoredox cobalt-catalyzed aromatic C—H thiolation for constructing C—S bonds, J. Am. Chem. Soc. 137 (29) (2015) 9273-9280.

[40] K. Lackey, M. Cory, R. Davis, S. V. Frye, P. A. Harris, R. N. Hunter, D. K. Jung, O. B. McDonald, R. W. McNutt, M. R. Peel, R. D. Rutkowske, J. M. Veal, E. R. Wood, The discovery of potent cRaf1 kinase inhibitors, Bioorg. Med. Chem. Lett 10 (3) (2000) 223-226.

[41] A. Rampa, L. Piazzi, F. Belluti, S. Gobbi, A. Bisi, M. Bartolini, V. Andrisano, V. Cavrini, A. Cavalli, M. Recanatini, P. Valenti, Acetylcholinesterase inhibitors: SAR and kinetic studies on omega-[N-methyl-N-(3-alkylcarbamoyloxyphenyl) methyl]aminoalkoxyaryl derivatives, J. Med. Chem. 44 (23) (2001) 3810-3820.

[42] R. Rossi Paccani, D. Donati, S. Fusi, L. Latterini, G. Farina, V. Zanirato, M. Olivucci, Toward a stable a-cycloalkyl amino acid with a photo switchable cationic side chain, J. Org. Chem. 77 (4) (2012) 1738e1748.

[43] D. A. Shapiro, S. Renock, E. Arrington, L. A. Chiodo, L. X. Liu, D. R. Sibley, B. L. Roth, R. Mailman, Aripiprazole, a novel atypical antipsychotic drug with a unique and robust pharmacology, Neuropsychopharmacology 28 (8) (2003) 1400-1411.

[44] A. Newman-Tancredi, S. Gavaudan, C. Conte, C. Chaput, M. Touzard, L. Verriele, V. Audinot, M. J. Millan, Agonist and antagonist actions of antipsychotic agents at $5HT_{1A}$ receptors: aGTPgS binding assay, Eur. J. Pharmacol. 355 (1998) 245-256.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A compound comprising Formula (I), (II), (III), or (IV):

(I)

wherein X is C=O or $CH_2$ and $R_1$ is AcHN or $NH_2$;

(II)

(III)

(IV)

wherein $R_3$ is Cl or H;
wherein $R_4$ is Cl, F, I, Br or H;
wherein $R_5$ is $CH_3$ or H;
wherein $R_6$ is =O, H or OH; and
wherein n is an integer from 1 to 3.

2. The compound of claim 1, wherein the compound comprises Formula (IV).

3. The compound of claim 2, wherein the $R_3$ is H.

4. The compound of claim 3, wherein the $R_4$ is Cl.

5. The compound of claim 4, wherein the $R_5$ is $CH_3$.

6. The compound of claim 5, wherein the $R_6$ is =O.

7. The compound of claim 6, wherein the n is 2.

8. A composition for treating a neurological disorder comprising:

a compound comprising Formula (I), (II), (III), or (IV):

(I)

wherein X is C=O or $CH_2$ and $R_1$ is AcHN or $NH_2$;

(II)

[Structure of formula (II): 3,4-dihydroquinolin-2(1H)-one with 6-O-propyl-piperazinyl-pyridine substituent]

(III)

[Structure of formula (III): indanone with 5-O-propyl-piperazinyl-pyridine substituent]

(IV)

[Structure of formula (IV): substituted indane with R3, R4, R5, R6 substituents and piperazinyl-pyridine substituent via (CH2)n linker]

wherein R₃ is Cl or H;
wherein R₄ is Cl, F, I, Br or H;
wherein R₅ is CH₃ or H;
wherein R₆ is =O, H or OH;
wherein n is an integer from 1 to 3; and
a pharmaceutically acceptable carrier.

9. The composition of claim 8, wherein the compound comprises Formula (IV).

10. The composition of claim 9, wherein the R₃ is H.

11. The composition of claim 10, wherein the R₄ is Cl.

12. The composition of claim 11, wherein the R₅ is CH₃.

13. The composition of claim 12, wherein the R₆ is =O.

14. The composition of claim 13, wherein the n is 2.

15. A method of treating a neurological disorder in a patient in need thereof comprising:
administering a therapeutically effective amount of a composition to a patient in need thereof, the composition comprising
a compound comprising Formula (I), (II), (III), or (IV):

(I)

[Structure of formula (I): phenyl ring with R1 substituent, X linker, propyl chain, piperazinyl-pyridine]

wherein X is C=O or CH₂ and R₁ is AcHN or NH₂;

(II)

[Structure of formula (II)]

(III)

[Structure of formula (III)]

(IV)

[Structure of formula (IV)]

wherein R₃ is Cl or H;
wherein R₄ is Cl, F, I, Br or H;
wherein R₅ is CH₃ or H;
wherein R₆ is =O, H or OH;
wherein n is an integer from 1 to 3; and
a pharmaceutically acceptable carrier.

16. The method of claim 15, wherein the neurological disorder is selected from the group consisting of depression, anxiety, schizophrenia, and cognitive deficits caused by Alzheimer disease.

17. The method of claim 15, wherein the compound comprises Formula (IV) wherein the R₃ is H and the R₄ is Cl.

18. The method of claim 17, wherein the R₅ is CH₃.

19. The method of claim 18, wherein the R₆ is =O.

20. The method of claim 19, wherein the n is 2.

* * * * *